United States Patent
Gilbert et al.

(10) Patent No.: US 9,658,125 B2
(45) Date of Patent: May 23, 2017

(54) FLUID CHARACTERISTIC INDICATOR

(71) Applicant: Right Biometrics, Scottsdale, AZ (US)

(72) Inventors: Paul J. Gilbert, Payson, AZ (US);
Rafal Chudzik, Peoria, AZ (US)

(73) Assignee: Right Biometrics, Scottsdale, AZ (US)

( * ) Notice: Subject to any disclaimer, the term of this patent is extended or adjusted under 35 U.S.C. 154(b) by 252 days.

(21) Appl. No.: 14/568,942

(22) Filed: Dec. 12, 2014

(65) Prior Publication Data
US 2015/0168244 A1 Jun. 18, 2015

Related U.S. Application Data

(60) Provisional application No. 61/915,151, filed on Dec. 12, 2013.

(51) Int. Cl.
*A61B 5/00* (2006.01)
*A61J 15/00* (2006.01)
*G01L 19/10* (2006.01)
*A61B 5/145* (2006.01)
*A61B 5/1473* (2006.01)
(Continued)

(52) U.S. Cl.
CPC .......... *G01L 19/10* (2013.01); *A61B 5/14539* (2013.01); *A61B 5/14735* (2013.01);
(Continued)

(58) Field of Classification Search
CPC ....... A61B 5/065; A61B 5/103; A61B 5/1032; A61B 5/1034; A61B 5/14539;
(Continued)

(56) References Cited

U.S. PATENT DOCUMENTS 3,373,735 A * 3/1968 Gallagher .......... A61B 5/14539
116/206
4,389,901 A * 6/1983 Lake ................... G01F 25/0007
73/861.58
(Continued)

FOREIGN PATENT DOCUMENTS

EP 2168558 3/2010
ES 2014890 A6 * 7/1990 ............... A61B 5/00
(Continued)

*Primary Examiner* — R. A. Smith
(74) *Attorney, Agent, or Firm* — Patti & Malvone Law Group, LLC

(57) ABSTRACT

A fluid characteristic indicator for measuring and indicating a characteristic of body fluid from a medical or veterinary patient has a tubular housing with suction and fluid inlet ports at opposite ends and a fluid characteristic indicating element disposed within. A diffuser supports the indicating element and has at least one fluid channel to direct fluid toward the indicating element. The fluid channel may be formed as a spiral or helix, or as a plurality of longitudinal fluid channels. The housing and the diffuser may have additional structures forming channels that cooperatively direct fluid toward the indicating element. The diffuser may occupy nearly all the interior volume of the housing. Control of the fluid flow may make exposure and saturation of the indicator more accurate, avoid spurious indications due to the color of the fluid itself, and reduce the amount of fluid sample needed to obtain an indication or measurement.

29 Claims, 23 Drawing Sheets

(51) Int. Cl.
*A61B 5/06* (2006.01)
*A61B 5/103* (2006.01)
*A61B 10/00* (2006.01)

(52) U.S. Cl.
CPC .......... *A61B 5/4238* (2013.01); *A61B 5/6852* (2013.01); *A61B 10/0045* (2013.01); *A61B 5/065* (2013.01); *A61B 5/1032* (2013.01); *A61B 10/007* (2013.01); *A61B 10/0051* (2013.01); *A61B 2010/0061* (2013.01); *A61J 15/0003* (2013.01); *A61J 15/0026* (2013.01); *Y10T 137/8158* (2015.04)

(58) Field of Classification Search
CPC ..... A61B 5/1473; A61B 5/14735; A61B 5/42; A61B 5/6852; A61B 10/00; A61B 10/0051; A61B 10/007; A61B 2090/0807; A61J 15/00; A61J 15/0003; A61J 15/0026; A61J 15/008; A61M 2016/0413; A61M 2025/0166; A61M 2205/3324; G01L 19/10; G01N 31/22
USPC .............. 116/206; 128/205.23, 207.14; 137/551–559; 422/85, 86, 87; 600/367
See application file for complete search history.

(56) References Cited

U.S. PATENT DOCUMENTS

| | | | | |
|---|---|---|---|---|
| 4,879,999 | A | * | 11/1989 | Leiman et al. ........ A61M 16/04 128/202.22 |
| 5,124,129 | A | * | 6/1992 | Riccitelli et al. . A61M 16/0488 128/207.14 |
| 5,166,075 | A | * | 11/1992 | Fehder ................. G01N 31/223 422/423 |
| 5,197,464 | A | * | 3/1993 | Babb et al. .......... G01N 31/223 128/205.23 |
| 5,291,879 | A | * | 3/1994 | Babb et al. .......... G01N 31/223 128/200.26 |
| 5,679,884 | A | * | 10/1997 | Kirk .................. A61M 16/0078 128/205.22 |
| 7,017,578 | B2 | * | 3/2006 | Tresnak et al. ... A61M 16/0488 128/200.26 |
| 9,173,602 | B2 | * | 11/2015 | Gilbert ................. A61B 5/6852 |
| 2013/0172781 | A1 | | 7/2013 | Russo |

FOREIGN PATENT DOCUMENTS

| | | | |
|---|---|---|---|
| WO | WO 9511716 A1 * | 5/1995 | ........... A61M 16/04 |
| WO | 2013025993 | 2/2013 | |

\* cited by examiner

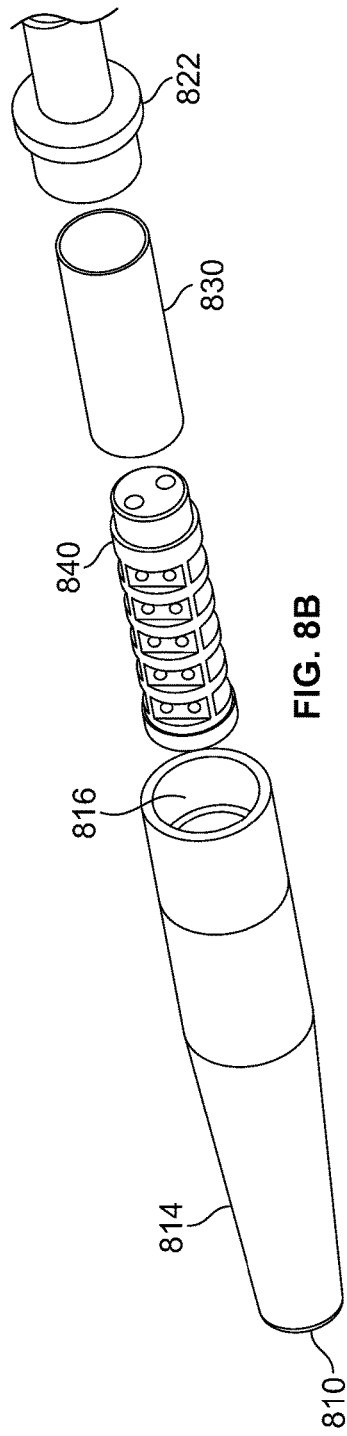
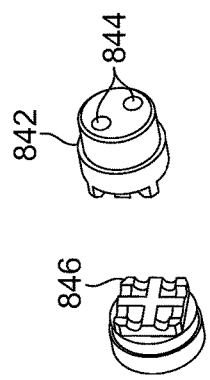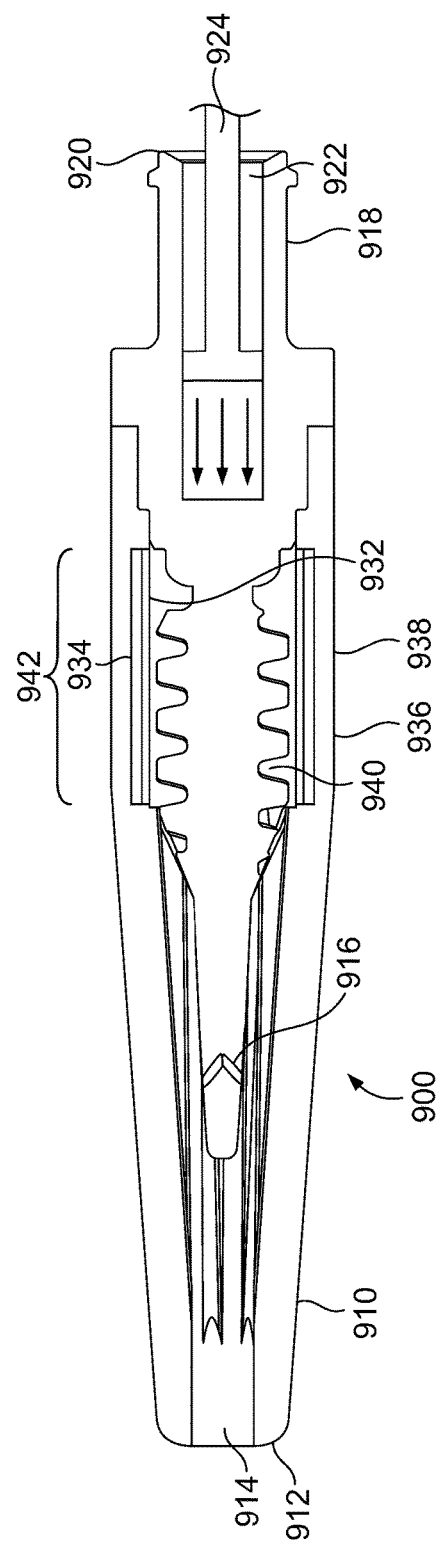

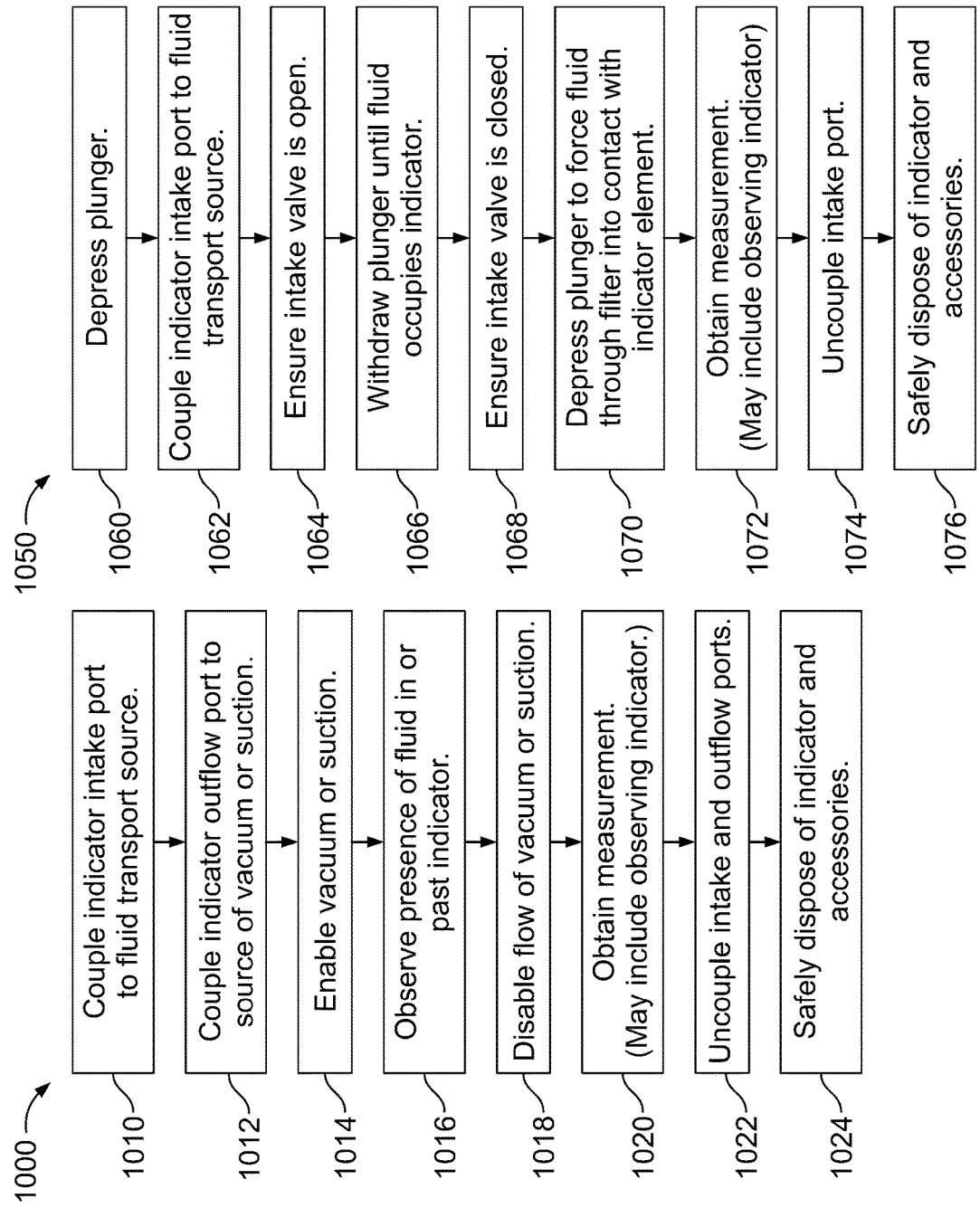

FLUID CHARACTERISTIC INDICATOR

CROSS REFERENCE TO RELATED APPLICATIONS

This application claims the benefit under 35 U.S.C. 119(e) of U.S. Provisional Application No. 61/915,151 filed 12 Dec. 2013, which is hereby incorporated by reference.

FIELD OF THE INVENTION

This application relates to apparatus and methods for measuring fluid characteristics, and more particularly to apparatus and methods for measuring and indicating a characteristic of a body fluid such as may be obtained from a medical or veterinary patient.

BACKGROUND OF THE INVENTION

Although a practitioner may obtain a sample of a fluid from a medical or veterinary patient and order a variety of laboratory tests thereon, the processing of the sample in the clinic, its transportation to the laboratory, processing and analysis in the laboratory, and reporting of results all cause delay and expense. In some cases, it is desirable for the clinician to obtain an immediate and reliable indication of one or more characteristics of a fluid obtained from a patient.

For example, when inserting a nasogastric tube, the tube may be undesirably positioned in the patient's lungs, instead of the stomach. Introduction of fluid which was intended to be introduced into the patient's stomach into the lung instead may be disastrous. However, correct insertion of the nasogastric tube in the stomach may be confirmed by aspirating fluid through the tube and measuring the pH of the fluid. A pH below 6 is characteristic of stomach fluid and signals the clinician that the tube has been correctly inserted.

Although there are a variety of supplies and equipment that could, in theory, be used in a clinical setting to measure a fluid characteristic, it is not always convenient or safe to perform reliable and accurate measurements. Test equipment may not necessarily be available in the clinic at the time it is needed, may require calibration or preparation of the equipment or accessories before use, cleaning after use, or non-trivial training of personnel for correct measurement, operation, and interpretation of the result. Also, the cost of some equipment makes it unaffordable in some clinics. The test results may be needed immediately, which can make obtaining and interpreting an accurate measurement challenging. Also, the sample itself may be unstable, either generally, over time, or as a result of exposure to air, test probes, containers, reagents, materials, or the like, which allows only limited time for performing a measurement. Some test equipment or procedures require that the sample be handled in the open, which can result in spills and exposure of personnel to the sample, which may present chemical, biological, or radiological hazards.

SUMMARY

There are disclosed herein several example embodiments of systems, apparatus, and methods for obtaining and containing a fluid obtained from a person or animal, measuring or detecting one or more characteristics of the fluid, and displaying an indication relating to the measurement. Also disclosed herein are methods of constructing and using such systems and apparatus. The person or animal may be, for example but without limitation, a medical, dental, or veterinary patient. The fluid, may be, for example but without limitation, a patient's body fluid, such as gastric aspirate, blood, urine, saliva, other fluids obtained from a patient's body, and the like. The indicators could also be used to measure characteristics of particulates, granules, powders, other solids, and the like, which can be transported in or with fluids, including gases, and the term fluid herein is intended to include fluids with entrained particulates, granules, powders, other solids, and the like.

In example embodiments, the indicator has a generally cylindrical housing with a distal port for receiving the fluid to be tested and a proximal port for connection to a source of suction. The housing, in cooperation with other components, forms a fluid chamber or passageway between the distal and proximal ports. An indicating element or medium sensitive to a fluid characteristic or property to be measured or sensed is disposed within the fluid passage and is arranged such that fluid present therein will contact the indicating element. The housing has a window or is otherwise transparent to allow the state of the indicating element to be observed from the outside, e.g., by a clinician. A reference indicator is provided on the outside of the indicator to allow comparison of the appearance or condition of the indicating element with reference examples corresponding to measurement results or other indicating element states of clinical significance. In some embodiments, the indicating element is a strip or cylinder of pH-sensitive paper which displays a color depending on the pH of a fluid to which the element is exposed; the reference indicator may, for example, indicate colors which the indicator element may display and the pH values corresponding thereto.

A diffuser and other internal structures control and condition the flow of the fluid in the indicator. The diffuser or at least a part thereof extends into the fluid chamber or passageway. In some examples, the diffuser has an indicating element section in proximity to the indicating element. The indicating element section has at least one fluid channel that directs fluid received at the distal port toward the indicating element. In one example, the fluid channel is in the form of a helix or spiral. In another example, a plurality of fluid channels is formed by a number of vanes, walls, or other structures extending longitudinally along the diffuser and radially from its center. The diffuser may also serve to support the indicating element.

Further, the diffuser may cooperate with the housing to control the flow of fluid as it approaches the indicating element section. For example, the diffuser may have an elongated tip that extends toward the distal port of the housing, which may, for example, have a generally conical tip. The interior surface of the housing, in the area of the distal port, may have a number of grooves or similar structures, which, in cooperation with the tip of the diffuser, form a plurality of fluid channels, e.g., extending longitudinally along at least a part of the distance between the distal port and the indicating element section.

In some embodiments, the diffuser is shaped and sized so as to fill almost the entire interior volume of the housing.

These characteristics of the diffuser structure and its cooperation with the housing, including the small infilled space in the interior of the indicator and the fluid pathways channeling and directing the flow of the fluid, may advantageously allow the indicator to produce a usable measurement with a smaller volume of fluid than would otherwise be required. Fluid is efficiently directed through the body using tracks, pathways and specific internal geometries that allow a very small volume of fluid to be transferred to the indicating element. In some examples, less than a drop of fluid is needed to initiate a color change.

In addition, the control of fluid flow may help avoid damage to the indicating element, which may be delicate, from forces imparted by fluid movement. In addition, the fluid pathways provided by the diffuser and the housing allow the indicator element to be exposed from the interior surface. This helps segregate the fluid on interior side of the indicating element, so that the indicator element is not viewed through the fluid. Gastric fluid often has a color (which may, for example, be caused by the presence of blood or other materials) and the color of the aspirate may affect the color change of the indicating element. Allowing the fluid to contact the indicating element from the reverse or interior, non-viewed side, prevents transfer of the color of the aspirate itself to the indicating element. This may advantageously prevent the color of the fluid under test or contaminants therein from affecting the measurement or indication.

In some embodiments, a filter is provided to limit exposure of the indicating element to fluid contents that may spuriously affect the indication is provides. For example, the filter may prevent materials that might otherwise impart a color change, other than that produced by the intended color reaction or other measurement indication of the indicating element, from reaching the indicating element.

In some embodiments, the diffuser is wholly contained within the indicator housing.

In some embodiments, the diffuser serves as the closure or end cap at the proximal end of the indicator and extends into the fluid chamber or passageway. A connection tube section of the diffuser serves as the proximal port of the indicator. A set of supports mechanically connect the connection tube section to the indicating element section of the diffuser. The connection tube section thus forms a part of the fluid passageway or chamber. The supports divide the fluid passageway into sections, e.g., quadrants. The sectionalization of the fluid passageway may advantageously evenly split the vacuum pressure coming from the syringe or other vacuum source to ensure that the fluid is aspirated evenly through the device.

In operation, the fluid enters the device through the distal port, which may be conical tip. In some examples, the fluid gets evenly separated by passing through plural symmetrical channels on the outer edge of the inner diameter of the housing. This smooths out the flow and allows the fluid to not clog the device. The channels direct the fluid toward the indicator element section of the diffuser. This ensures that the fluid travels down the predetermined pathway to maximize efficiency Once the fluid enters the fluid channels of the diffuser, it is directed in an outward direction. As the fluid is moved away from the center of the device, it comes in contact with the interior or reverse side of the indicator element. Also, as the fluid comes in contact with the indicator element, it exposes or saturates the element from the distal to proximal end and inside to out. This directional saturation may advantageously result in faster and more accurate saturation with very low fluid volume. In examples where the diffuser fluid channel has the form of a spiral, fluid is directed centrifugally from the center of the body to the outside.

In some examples, the indicating element may reside in a removable container. In some examples, a plurality of indicating elements may be reside in a cassette or other removeable container. These examples allow the indicating element to be replaced or renewed without discarding or disconnecting the indicator. In some examples, a plurality of indicating elements are present, selected ones of which may be exposed to the fluid under test.

BRIEF DESCRIPTION OF THE DRAWINGS

FIG. 8B is an exploded view of the indicator 800 of FIG. 8A;

FIG. 8C is an exploded view showing two instances of blocks 842 which may be used in the indicator 800 of FIGS. 8A and 8B;

FIG. 9 is a cross-section view of another example embodiment 900 of an indicator constructed according to a further aspect of the invention, in which the indicator provides a filter to filter the fluid to which the indicator element is exposed;

FIG. 10A is a flow chart of an example embodiment of a method 1000, according to an aspect of the invention, which may be used in conjunction with embodiments of indicators of the types disclosed herein for obtaining a measurement or detection;

FIG. 10B is a flow chart of a further example embodiment of a method 1050, according to an aspect of the invention, which may be used in conjunction with embodiments of indicators of the types disclosed herein for obtaining a measurement or detection;

DETAILED DESCRIPTION

There are disclosed herein several example embodiments of systems, apparatus, and methods for obtaining and containing a fluid obtained from a person or animal, measuring or detecting one or more characteristics of the fluid, and displaying an indication relating to the measurement. Also disclosed herein are methods of constructing and using such systems and apparatus. The person or animal may be, for example but without limitation, a medical, dental, or veterinary patient. The fluid, may be, for example but without limitation, a patient's body fluid, such as gastric aspirate, blood, urine, saliva, other fluids obtained from a patient's body, and the like. The term fluid is intended to include, without limitation, liquids, gases, mucous, gels, and may also include other matter amenable to handling in nasogastric tubes, feeding tubes, suction tubes, or similar tubing found in hospitals, physician, veterinarian, and dental offices, and other clinical settings. The indicators could also be used to measure characteristics of particulates, granules, powders, other solids, and the like, which can be transported in or with fluids, including gases, and the term fluid herein is intended to include fluids with entrained particulates, granules, powders, other solids, and the like.

Figure 1C:
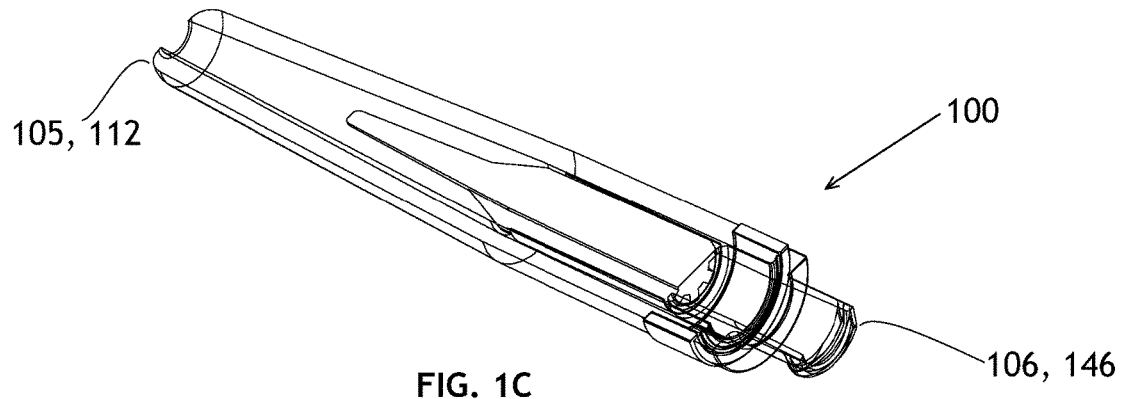
FIG. 1C is a half-sectioned view of the indicator 100 of FIGS. 1A-1B.
Figure 1B:
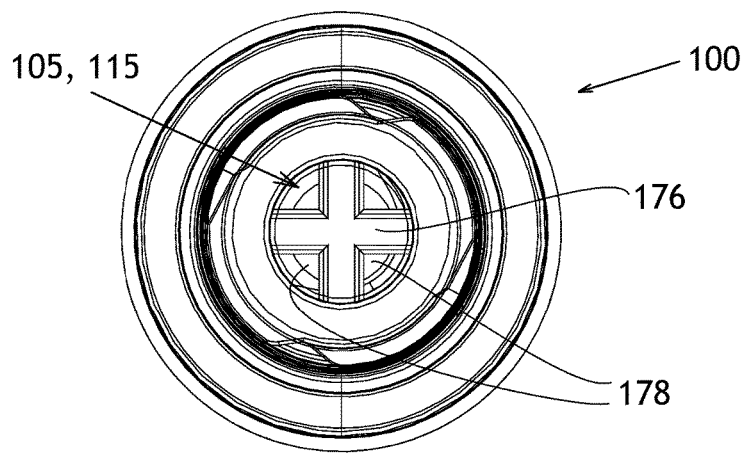
FIG. 1B is an end view of the indicator 100 of FIG. 1A, looking toward the proximal end thereof.
Figure 1A:
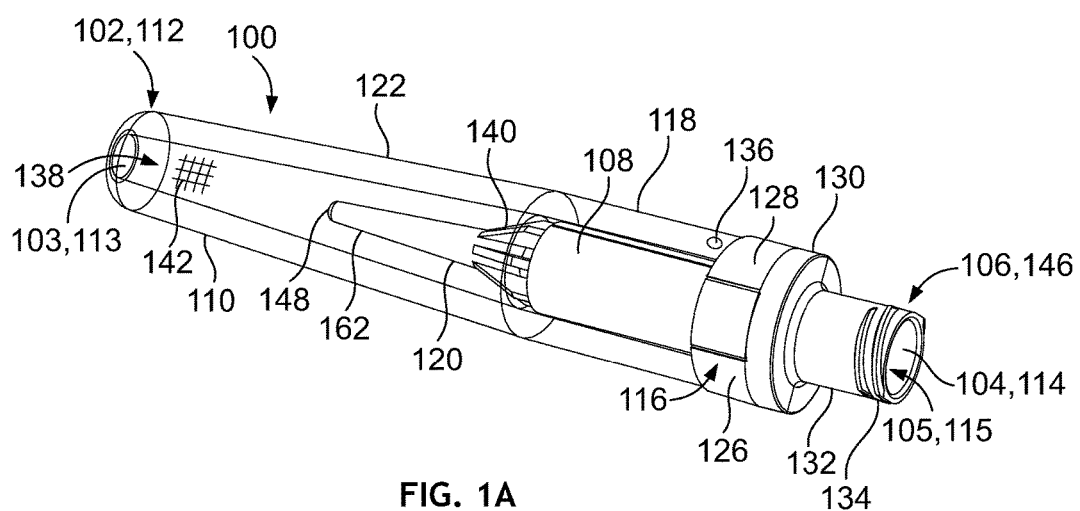
FIG. 1A is an isometric view of a first example embodiment 100 of apparatus for obtaining and containing a fluid obtained from a person or animal, measuring or detecting one or more characteristics of the fluid, and displaying an indication relating to the measurement, constructed according to an aspect of the present invention.
Figures 1D, 1E:
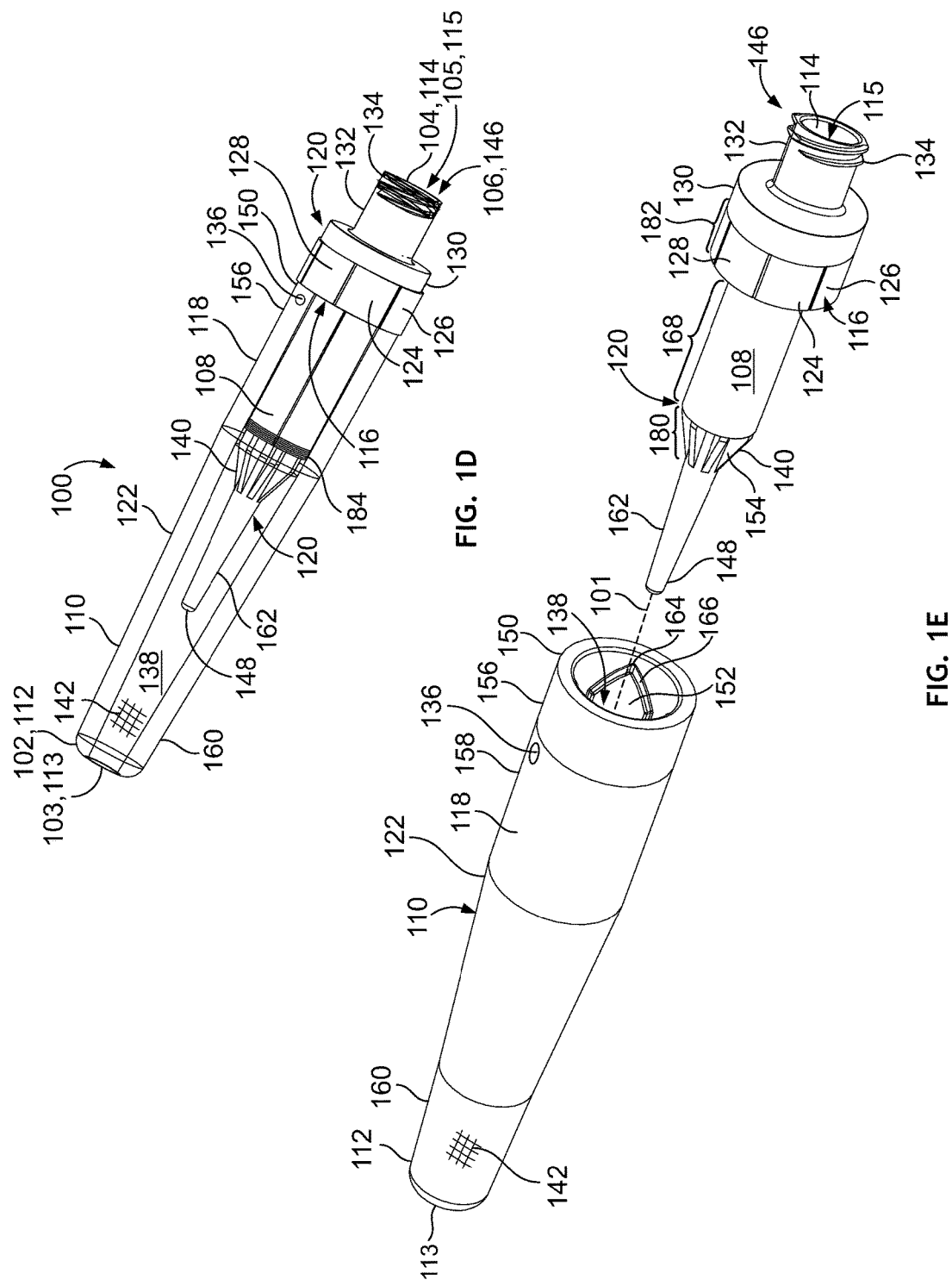
FIG. 1D is a further isometric view of the indicator 100 of FIGS. 1A-1D, taken from a different angle.
FIG. 1E is a partial exploded view depicting the housing 110 and diffuser 120 components of indicator 100 separately, for example, as they might appear prior to assembly as a unit.

FIG. 1A is an isometric view of a first example embodiment 100 of apparatus for obtaining and containing a fluid obtained from a person or animal, measuring or detecting one or more characteristics of the fluid, and displaying an indication relating to the measurement, constructed according to an aspect of the present invention, which apparatus may be referred to hereinafter as indicator device 100 or indicator 100. FIG. 1B is an end view of the indicator 100 taken from the proximal end 104 thereof. FIG. 1C is a half-section view of the indicator 100. FIG. 1D is another isometric view of indicator 100 taken from a different angle.

As best seen in FIGS. 1A-1D, indicator 100 preferably has a generally tubular shape having a distal end 102 and a proximal end 106. The indicator 100 has a distal-end or intake port 103 at the distal end 102, and a proximal-end or outflow port 104 at the proximal end. A fluid communication chamber, lumen, or passage 105 extends between the ports 103 and 104 and permits flow of fluid therethrough. An indicating element or medium 108 sensitive to a fluid characteristic or property to be measured or sensed is disposed within fluid passage 105 and is arranged such that fluid present therein will contact indicating element 108. The fluid passage 105 may include various volumes, spaces, conduits, channels, chambers, and the like in fluid communication within the indicator 100. An indicator window portion 118, which is preferably substantially transparent, is provided in the indicator 100 to render the indicating element 108 externally visible or observable. In general operation, the distal end port 103 of the indicator is coupled for fluid communication with a source, conduit, or reservoir of or containing a patient's body fluid or other fluid to be tested, which source may, for example, be a nasogastric tube or feeding tube inserted into the patient's stomach, or a suction tube in use in treating or diagnosing the patient. The proximal end port 104 is coupled to a source of vacuum or suction so as to draw or aspirate fluid through distal end port 103 into passage 105 and into contact with or in the vicinity of the indicating element 108. Responsive to the contact with or the presence of the fluid, the indicating element 108 may exhibit an externally observable indication, or change therein, relating to the fluid characteristic or property to be sensed or measured. For example but without limitation, the indicating element 108 may be a pH-indicating paper which presents a color or shade or other visible indicia corresponding to the pH of the fluid, or a range thereof, or the value of the characteristic on one side or the other of a defined threshold. Indicating elements or media of other types, or sensitive to other fluid characteristics or properties, could also be used, as discussed further.

As best seen in FIGS. 1A-1D, indicator 100 preferably comprises a housing 110 and a diffuser element 120, a portion of which is telescoped into housing 110. FIG. 1E is a partial exploded view depicting the housing 110 and diffuser 120 components of indicator 100 separately, for example, as they might appear prior to assembly as a unit, by telescoping a distal end 148 of diffuser 120 into an opening or chamber 152 at the proximal end 150 of the housing as shown by broken line 101. Although an embodiment of indicator 100 may be constructed by so assembling the housing 110 and diffuser 120, indicator 100 could also be constructed in other ways that may not require the housing 110 and diffuser 120 to exist as separate elements which are later joined. The subsequent description of the indicator 100 may best be understood by considering, in conjunction, FIGS. 1A-1E.

Housing 110 is constructed as a generally tubular or barrel shaped body, which has a distal end 112, and a proximal end 150. The housing 110 has, adjoined in series from proximal end 150 to distal end 112, a first section 156, a second section 158 including the indicator window 118, a third or central section 122, and a fourth section 160. These sections are not necessarily separate parts or components, although they could be, and are identified for ease of reference to structure or function. The housing has a distal opening or intake port 113 at the distal end 112, and a proximal opening or port 152 at the proximal end 150, which are joined by an interior central fluid communication chamber, lumen, or passage 138 extending generally longitudinally between the ports 152 and 113. In the assembled form of indicator 100, housing fluid passage 138 serves as the distal portion of indicator fluid passage 105, and housing distal port 113 serves as the indicator distal port 103. The fluid passage 138 may include various volumes, spaces, conduits, channels, chambers, and the like in fluid communication within the housing 110, and may include all or less than all of the open interior space in the housing not occupied by solid materials.

Housing 110 preferably has a first diameter at first section 156 and second section 158 to receive a portion of diffuser 120. Housing 110 may have at fourth section 160 and distal end 112 a second diameter, relatively smaller than the first diameter. The diameter of fourth section 160 and distal end 112, and the shapes thereof, preferably allow fourth section 160 to mate, couple, or connect with a fluid transport source (not shown), which may take the form of tubing, conduits, adapters, appliances, containers, reservoirs, catheters, feeding tubes, suction tubes, or the like, which may be used in a clinical environment to furnish the fluid with which indicator 100 is to be used to perform a test, or obtain a measurement, or indication of one or more characteristic or property of the fluid. For example, the fourth section 160 and distal end 112 may have a diameter and be formed with a "catheter tip" shape suitable for mating, coupling, or connection with a catheter, such as a nasogastric tube or feeding tube which is inserted into a patient's stomach and which serves as the fluid transport source. The catheter tip can also be mated with other types of receiving connector, plugs, hubs, and the like.

Because vacuum or suction will typically be used to draw or aspirate fluid from the fluid transport source into the indicator 100, the mating, coupling, or connection between housing 110 and the fluid transport source preferably forms a substantially vacuum-tight seal at the vacuum or suction pressures used in a clinical environment. The indicator 100 could also be used in a mode where fluid under test is furnished from a source under some pressure, in which case the seal is preferably sufficient to avoid leakage of the fluid. The housing 110, or portions thereof, such as fourth section 160, which will mate or couple with a fluid transport source or adapter, may have a surface texture or treatment 142 that forms or enhances the seal. For example, the surface treatment 142 may be a flexible, resilient, or tacky coating that grips or adheres to a mating surface, such as the inside diameter, of the fluid transport source. Surface treatment 142 may also be implemented a pattern or texture on or in the surface of housing 110 that increases adhesion or local contact pressure between housing 110 and the fluid transport source, or otherwise enhances the seal. For example, the surface treatment 142 may be constructed as one or more circumferential ridges disposed near distal end 112, but could also be any other suitable pattern or texture, including hatching, a random or pseudo-random texture, or the like.

Although housing 110 is depicted in FIGS. 1A-1E, with a "catheter tip" distal end 112 configuration that accommodates frictional, sealing engagement with the fluid transport source, housing 110 could also have another structure for coupling to the fluid transport source. FIG. 2A is a side view of an embodiment 170 of a housing constructed in accordance with a further aspect of the present invention. Housing 170 is generally similar to the housing 110 of FIGS. 1A-1E, but has a male Luer lock fitting 174 at the distal end 172, instead of the catheter tip. Housing 170 is generally similar to housing 110 of FIGS. 1A-1E as heretofore described, and except for the differences explained below, the foregoing description of housing 110 housing 170, mutatis mutandis, and is hereby incorporated by reference. The Luer lock 174 may mate with a complementary fitting on the fluid transport source. The positive mating avoids the need to rely on friction alone for a seal and may avoid malfunction or spills when tension applied between the indicator 100 or the fluid transport source may tend to separate these components. Any other appropriate coupling or fitting could also be used. Thus, in constructing an embodiment of indicator 100, housing 170 of FIG. 2A may be substituted for housing 110.

Alternatively, an adapter, such as the adapter 700 of FIGS. 7A-7G, discussed further below, could be used to make the coupling between distal end 112 and a fluid transport source having a Luer lock or similar fitting.

As a further alternative, any of the housings described herein could have a port with an appropriate puncturable seal for use with a sample collection appliance of the type typically used in clinical settings for collection of blood samples. Such appliances typically have a cup-shaped receptacle with a two-ended hollow needle extending in both directions from the closed end of the cup. In typical use in collecting a blood sample from a patient, the outward-extending end of the needle is inserted into the patient's vein. An evacuated test tube with a puncturable seal is then inserted, seal-end first, into the cup, so that the inward-extending end of the needle punctures the seal. Because the test tube is evacuated, blood is drawn through the needle into the test tube. When an adequate sample of blood has been acquired, the test tube is removed from the cup, and the seal recloses around the puncture. The appliance may then be removed from the patient. A similar seal could be provided on the distal end of any of the housings described herein, so that the associated indicator may be used with the aforementioned sample collection appliance in the same manner as a sample test tube. Moreover, the proximal end port may be sealed or omitted, and the indicator could be evacuated, so that when the indicator is inserted into the cup of the sample collection accessory, puncturing the seal, the partial vacuum draws blood through the needle into the indicator, without requiring an external source of vacuum or suction.

As best seen in FIGS. 1A-1E, third or central section 122 may provide a tapering transition from the smaller diameter fourth section 160 to the larger diameter second section 158 and first section 156. The section of fluid passage 138 that extends through third or central section 122 may also have an interior diameter that is similarly tapered, accommodating the tapered shape of the tip section 162 of diffuser 120 which extends through fluid passage 138 in the area of the central section 122. As will be described further in greater detail, among the functions of the diffuser 120 are to control the distribution of fluid that enters the indicator 100 at the distal end port 103, 113 to the indicating element 108. In some cases, the diffuser 120 may have one or more of these functions: to divide, render uniform or otherwise optimize the fluid distribution to the indicating element 108, to maximize contact of the fluid with the indicating element 108, to maximize exposure or saturation of as much of the indicating element 108 as possible, to cause exposure or saturation of the entire indicating element 108 to occur simultaneously, or in a controlled progression from distal to proximal ends, to the greatest extent possible, or to filter the fluid so as to exclude or preferentially route or direct components thereof toward the indicating element. The diffuser 120 may have additional functions. In an example embodiment of the housing 110 constructed according to an aspect of the invention, the portion of the fluid passage 138 in the area of central section 122 is a generally coaxial channel formed as the space between the tapered diffuser tip section 162 and the interior surface of central section 122.

The second section 158 of housing 110 preferably contains an indicator window 118 which is substantially transparent to allow observation of the indicating element 108 disposed in the interior of housing 110. As described below in greater detail, in some embodiments, the indicating element 108 may be a tubular or cylindrical and may be generally coaxial with the body of housing 110 and the diffuser 120, in which case it may be preferable that the indicator window 118 allow observation at any angle about the general longitudinal axis of the indicator 100. The indicator window 118 may, for non-limiting example, be realized by constructing section 158, or some longitudinal extent thereof, from a transparent material, which would afford observation from any angle about the longitudinal axis. However, in some embodiments, indicating element 108, or the measuring, sensing, or indicating part thereof, may be occupy a full circumference around the general longitudinal axis. For example, the indicating element 108 could be constructed as a strip or dot of indicating medium that appears only on one side (or some other limited angular extent) of diffuser 120. In that case, section 158 may have a smaller indicator window 118 configured to ensure that the location of the indicating element 108 is conspicuously visible through the window 118, to avoid erroneous readings that could occur if the user mistakes some other internal component as the indicating element 108. In some cases, fluid or air flow through the device, or handling of the device, may tend to dislodge the indicating element from a preferred location with respect to the indicator window or other elements. It is generally desirable that the indicating element not move when the indicator is in use. A retaining shoulder 184 of reduced diameter (i.e., extending inward) may be provided on the interior surface of the housing 110 near the distal end of the first section 156 to prevent undesired migration of the indicating element 108. The retaining shoulder 184 may, for example, have a radial thickness of approximately 0.010 in. The indicating element could also be secured or fixed in location with respect to the housing using other structures such as tabs, clips or burrs, adhesive attachment, other chemical attachment means, thermal, chemical, or ultrasonic welding, or any other appropriate securement means. The retaining shoulder 184 or other indicating element retaining means may be used on any of the housings described herein.

A port 136 may be provided on a portion of the housing 110 to allow fluid to be withdrawn, e.g., for other testing, examination, treatment, diagnosis, or procedures. The port 136 also allows reagents, dies, other chemicals, or other material to be added. This could be used, for example, where the indicator may furnish a measurement only with the added material, or where the indicator may furnish an additional useful measurement, or additional precision in measurement, after the added material. The port 136 may be by a puncturable seal, so that material may be added or removed via a needle and syringe or the like, and the seal may be a self-reclosing seal to avoid leakage in or out through the port after use.

According to a further aspect of the invention, the housing central fluid communication chamber or passage may have a modified cross section to cooperate with the diffuser 120 to distribute fluid to the indicating element 108.

Figure 2B:
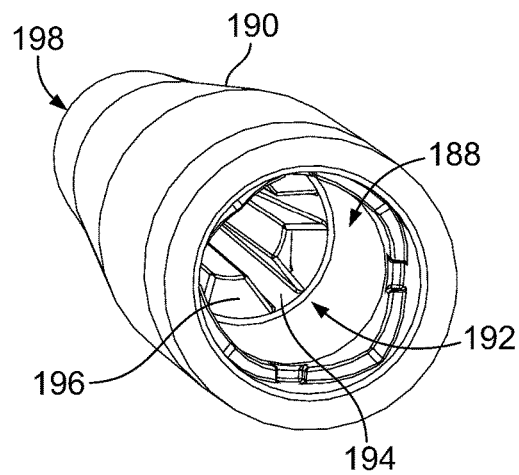
FIG. 2B is an isometric view of a further embodiment 190 of a housing according to an aspect of the present invention, which housing provides a central fluid passage of modified cross section.
Figure 2A:
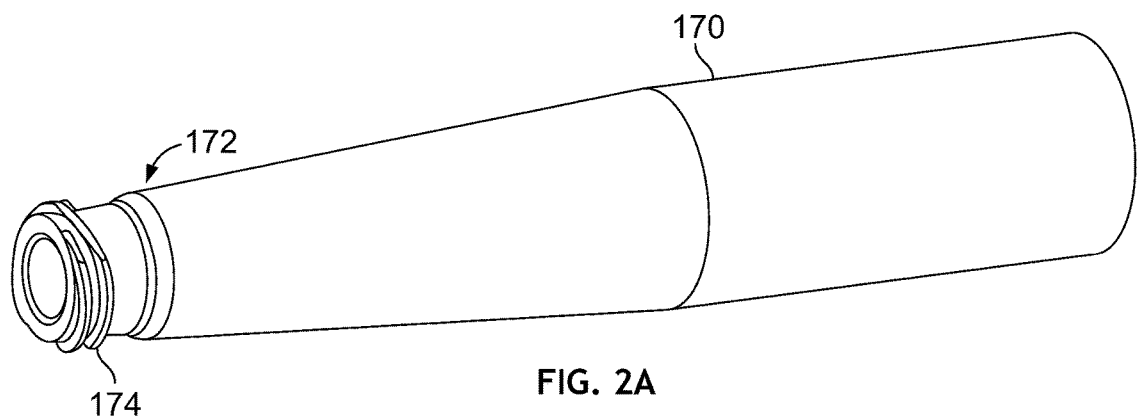
FIG. 2A is a side view of a housing 170 of a further example embodiment of a body fluid characteristic indicator, according to a further aspect of the invention, the housing having a male Luer lock fitting at the distal end thereof.
Figure 2C:
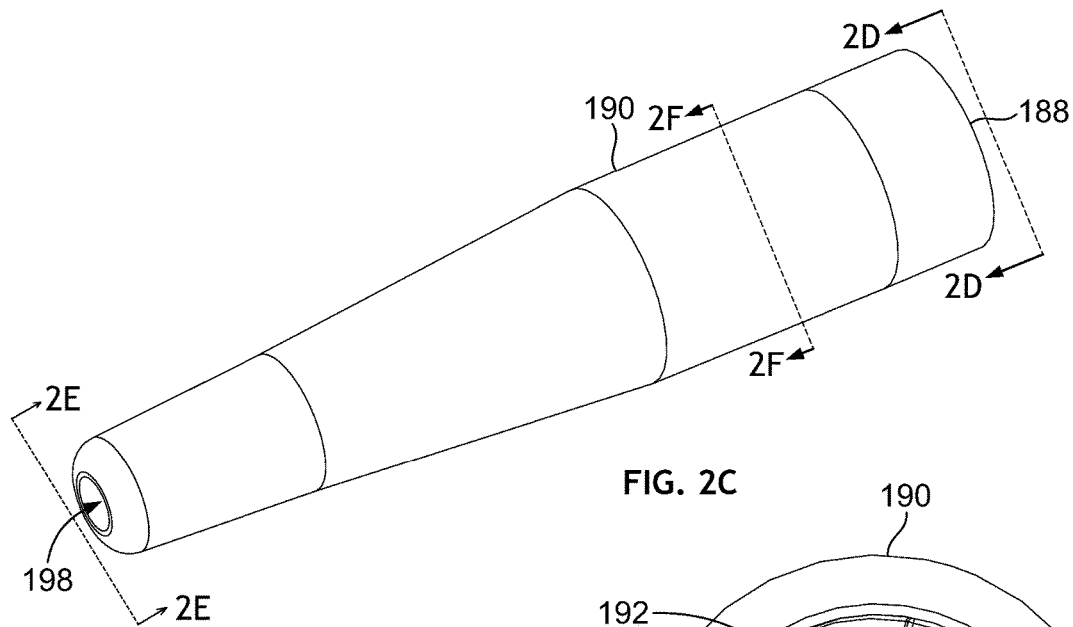
FIG. 2C is a side view of the housing 190 of FIG. 2B.
Figure 2D:
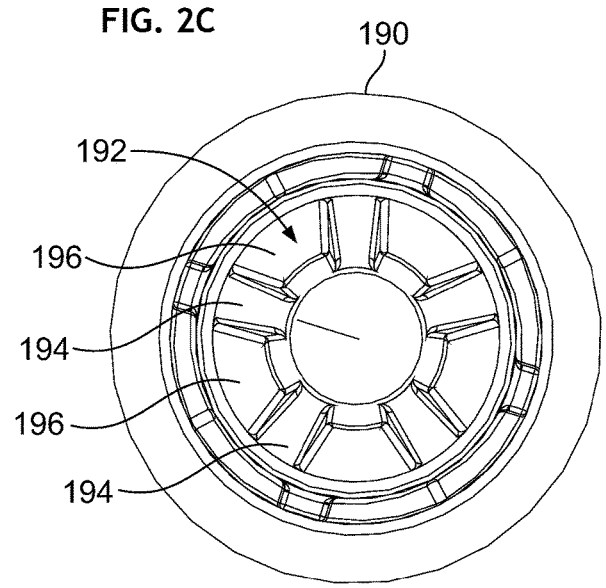
FIG. 2D is a view of housing 190 of FIGS. 2B-2C looking into the proximal end opening 188 as shown by view lines 2D-2D of FIG. 2C.
Figure 2E:
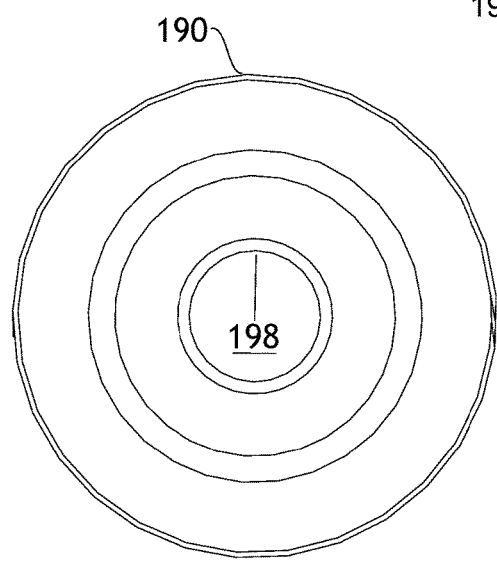
FIG. 2E is a view of housing 190 of FIGS. 2B-2D looking into the distal end opening 198 as shown by view lines 2E-2E of FIG. 2C.
Figure 2F:
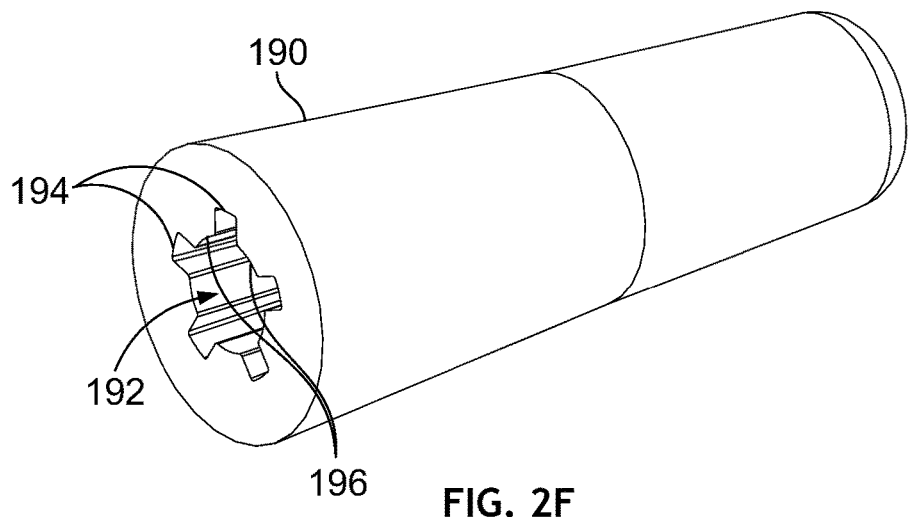
FIG. 2F is a cutaway view of the housing 190 of FIGS. 2B-2E, taken along the view lines 2F-2F of FIG. 2C.

FIG. 2B is an isometric view, and FIG. 2C is a side view, of a further embodiment 190 of a housing which is similar to the housing 110 of FIGS. 1A-1E but which provides a central fluid passage 192 of modified cross section. Housing 190 is generally similar to housing 110 of FIGS. 1A-1E as heretofore described, and except for the differences explained below, the foregoing description of housing 110 is applicable to housing 190, mutatis mutandis, and is hereby incorporated by reference. A fluid passage 192, which functions in a manner similar to the fluid passage 138 of the housing 110 of FIGS. 1A-1E extends between a distal-end intake port 198 and a proximal end opening 188. FIG. 2D is a view of housing 190 looking into the proximal end opening 188 as shown by view lines 2D-2D of FIG. 2C. FIG. 2E is a view of housing 190 looking into the distal end opening 198 as shown by view lines 2E-2E of FIG. 2C. FIG. 2F is a cutaway view of the housing 190 of FIGS. 2B and 2C, taken along the view lines 2F-2F of FIG. 2C.

As best seen in FIGS. 2B, 2D, and 2F, housing 190 has a plurality of inward-facing ribs 196 extending radially inward into fluid passage section 192, and extending longitudinally along at least a portion of the housing 190. The longitudinal ribs 196 form a plurality of complementary longitudinally-extending fluid channels 194. The diffuser tip section 162 and the longitudinal ribs 196 may be sized to substantially fill the fluid passage 192 except for the fluid channels 194, to force all the fluid to pass through the fluid channels 194. Alternatively, the diffuser tip section 162 and longitudinal ribs 196 may be sized to allow space therebetween, providing as part of fluid passage 192 an additional coaxial channel for fluid flow that extends longitudinally along housing 190. These geometries and spacing may be adapted to accommodate expected characteristics of the fluid, such as viscosity, the presence of solids, or the like. In constructing an embodiment of indicator 100, housing 190 may be substituted for housing 110. The configuration of the fluid channels 194 tends to promote laminar flow of the fluid as it approaches the indicating element 108. Laminar flow may help regulate suction, and may help control the consistency or filtration of the fluid or its components. In addition, laminar flow can reduce the risk of washing off or otherwise removing components of the indicator element, such as dies, and can reduce the risk of damaging the indicator element, which may be fragile. All of these risks may be higher when turbulent fluid flow is present.

As best seen in FIGS. 1A-1E, diffuser 120 has a proximal end 146 and a distal end 148. In some embodiments according to an aspect of the invention, indicator 100 is assembled by telescoping the distal end 148 of the diffuser 120 into the proximal-end opening 152 of housing 110. In those embodiments, the diffuser 120, or one or more portions thereof, functions as a closure or end cap for the housing 110, and further provides a proximal end opening or outflow port 114 into a fluid communication chamber, lumen, or passage 115. In the assembled configuration of indicator 100, diffuser fluid passage 115 serves as the proximal portion of indicator fluid passage 105, and diffuser proximal port 114 serves as the indicator proximal port 104. The fluid passage 115 may include various volumes, spaces, conduits, channels, chambers, and the like in fluid communication within or adjacent to the diffuser 120. In the assembled configuration of indicator 100, port 114 is in fluid communication via fluid passage 115 with the interior volume and fluid passage 138 of housing 110. In typical operation, proximal end port 104, 114 is connected to a source of suction or vacuum so as to draw fluid under test through distal end port 103, 113, housing fluid passage 138, and into the region of the indicating element 108. Port 104, 114 preferably has an appropriate fitting 134 for secure connection to a tube or conduit coupled to a source of suction or vacuum. For example, fitting 134 may be male Luer lock fitting. Other fittings could also be used.

In some cases, the diffuser 120 may have one or more of these functions: to divide, render uniform or otherwise optimize the fluid distribution to the indicating element 108, to maximize contact of the fluid with the indicating element 108, to maximize exposure or saturation of as much of the indicating element 108 as possible, or to cause exposure or saturation of the entire indicating element 108 to occur simultaneously, or in a controlled progression from distal to proximal ends, to the greatest extent possible. Thus, the structure and configuration of diffuser 120, and its relationship to housing 110, may provide these and other functions in various embodiments.

Diffuser 120 has a generally longitudinal body comprising, in series starting at the proximal end 146, a connection tube section 132, a reference indicator retaining collar 130, a first transition section 182, indicating element section 168, a second transition section 180, a tip section 162, and distal end 148. The connection tube 132 forms the proximal end of diffuser fluid passage 115. Fluid passage 115 continues toward the distal end of diffuser 120 as a generally tubular structure interior of and through the collar 130 and the first transition section 182 into the volume contained by the housing 110. Thus, fluid passage 115 couples port 104, 114 to the housing fluid passage 138.

The indicating element section 168 of the diffuser 120 preferably has one or more fluid-channel-forming structures 140 to support the indicating element 108 and to distribute fluid entering the indicator 100 and housing 110 at the distal end 102, 112 and port 103, 113 thereof to the indicating element 108. The fluid-channel-forming structures 140 form one or more fluid channels 154 which are operatively coupled to fluid passage 115.

The second transition section 180 (FIG. 1E) guides fluid from the portion of housing fluid passage 138 in the area of diffuser tip section 162 into the diffuser fluid channels 154.

In operation, the vacuum or suction coupled via port 104, 114 draws fluid via the fluid passage 138 into fluid channels 154 and into contact with or in the vicinity of the indicating element 108. Under influence of the suction or vacuum, the fluid continues through first transition section 182 and connection tube 132 and exits to the suction or vacuum system or reservoir. In an embodiment where the indicating element 108 is a tube or similar structure surrounding the fluid-channel-forming structure 140 of indicating element section 168, the fluid must travel through the diffuser fluid channels 154 to reach the exit, and accordingly, the fluid must come into contact with or in the vicinity of the indicating element 108. If the indicating element is generally pervious to the fluid, the fluid may pass through the indicating element 108. In an initial stage of operation, the fluid transport source and the indicator 100 may be filled with air, which, during continued operation, is eventually replaced by the fluid under test.

In an embodiment 120 of a diffuser constructed according to one aspect of the invention, the indicating element section 168 may have a generally star-shaped cross-section formed by spines, ridges, or vanes 140 extending radially from a central core along the length of indicating element section 168. The vanes 140 further extend longitudinally between the indicating element section 168 to the tip section 162 through the second transition section 180, tapering in diameter. The configuration of vanes 140 form plural substantially independent diffuser fluid channels 154, which may be used to independently expose different indicating elements 108 or portions thereof. The plural independent diffuser fluid channels 154 could also be used to route fluid from different respective fluid sources to one or more indicating elements; a modification of the housing would be needed to receive fluid from plural sources and separately convey the fluid to respective fluid channels. Other diffuser configurations may also be used, as discussed further.

The indicating element 108 is preferably disposed adjacent to the fluid-channel-forming structure 140 of indicating element section 168, and the diffuser fluid channels 154 formed thereby. For example, indicating element 108 may be implemented as a tubular component arranged around the fluid-channel-forming structure 140. The indicating element 108 may be constructed as a tube, but could also be a sheet wrapped around the fluid-channel-forming structure 140. Indicating element 108 could take other suitable forms, such as strips, ribbons, dots, bars, or the like, and in those forms are preferably disposed adjacent the fluid-channel-forming structure 140 and the diffuser fluid channels 154 formed thereby.

A reference indicator 116 is preferably provided on the diffuser 120 adjacent collar 130. The reference indicator 116 may be constructed as a generally tubular element disposed coaxially around the body of diffuser 120, overlapping the first transition section 182. In the assembled configuration of indicator 100, the reference indicator may coaxially overlap the first section 156 of housing 110 and is preferably adjacent to the indicator window 118 of the housing, so that the reference indicator 116 may be directly compared with the indicating element 108. The reference indicator 116 preferably bears suitable indicia which may be compared with indications displayed by the indicating element 108 to represent a measured value or state of a characteristic or property of the fluid under test.

For example, in an embodiment where the indicating element 108 is a pH-indicating paper that indicates the measured pH by a corresponding color, the reference indicator 116 may contain a plurality of labeled color samples or indicia, such as 124, 126, and 128, against which the indicating element 108 may be compared by a user to obtain a pH measurement. Although three color samples are depicted in the figures, it will be appreciated that any number of color samples or indicia may be provided to accommodate the range of indications of which the indicating element 108 is capable and to accommodate the desired precision of measurement.

The reference indicator 116 may contain other indicia as appropriate for the type of indicating element 108 being used and the fluid characteristic or property (or a plurality thereof) to which the indicating element 108 is sensitive. For example, in some embodiments, the indicating element 108 could distinguish fluid characteristics or properties by displaying shapes, letters, icons, or other symbols instead of colors, and the reference indicator 116 could present reference examples of the symbols for comparison. Reference indicator 116 may also provide a legend or other indicia which may, for example, be used to interpret the symbols or other indicia displayed by indicating element 108.

While is it usually desirable that the entire indicating element 108 be uniformly saturated with the fluid under test, characteristics of the fluid, or limited availability of the fluid, could result in only a limited extent of the indicating element 108 being exposed or providing a useful indication of the measured fluid characteristic or property. Also, in some embodiments, indicating element 108 may not be present or visible throughout all angles about the general longitudinal axis of indicator 100. Further, in some embodiments, plural indicating elements (or plural portions of a single indicating element) sensitive to different characteristics or properties may be visible at respective properties about the axis. Reference indicator 116 is preferably rotatable so that any of its samples or indicia may be brought into juxtaposition with a visible portion of indicating element 108 through indicator window 118 to enable comparison of the indication with the reference sample or indicia.

In an embodiment in which indicator 100 is constructed by assembling the diffuser 120 telescopically into the proximal-end opening 152 of the housing 110, it is preferable that in the assembled configuration the diffuser 120 occupy desired longitudinal and angular positional relationships with respect to the housing 110. Housing 110 preferably has one or more locator structures 164 which help ensure the that the desired positional relationships will be achieved in the assembly process. The locator structures 164 may be formed as tabs or other sections of reduced inside diameter of the housing in the area of the proximal-end opening 152. The locator structures 164 cooperate with locator structures on the diffuser. (See, for example, locator structures 320 of FIG. 3F.) For example, the locator structures may be formed as tabs or other sections of increased outside diameter on a telescoping segment of the diffuser 120, having a shape or profile that complements or mates with the shape of locator structures 164. In one embodiment constructed according to an aspect of the invention, the locator structures on at least one of the housing 110 and the diffuser 120 provide a substantially triangular socket for receiving the mating structure of the other component, as best seen in FIG. 1E. The use of the triangular mating shapes allows the components to self-align, with respect to their angular position, during telescopic assembly. This reduces or eliminates the need to begin assembly with the components in a specific angular alignment. The locator structures 164 and, and complementary locator structures on the diffuser, preferably have respective interference faces which, upon completion of the telescopic assembly, oppose one another and are in secure contact with one another. For example, locator structures 164 of housing 110 has interference faces 166. The locator structures and interference faces thereof of diffuser 120 are not visible in FIGS. 1A-1E, but similar locator structures 320 and locator structure interference faces 324 are provided on diffuser 310 (see FIG. 3F).

In embodiments in which the housing 110 and diffuser 120 are assembled to form the indicator 100, in addition to its other functions, the diffuser 120 or a portion thereof may function as a closure or end cap for the housing 110, and therefore, it is desirable that a seal be formed between the housing 110 and the diffuser 120. The seal could be formed at any interfaces of these components. Where a seal depends on contact between mating or abutting surfaces, the contact may be a tight, friction or interference contact to achieve an effective seal. In an embodiment constructed according to an aspect of the invention, the seal may be formed where a collar of the diffuser 120 is in contact with the surface of the proximal end 150 of the housing. The seal may also be formed where the outer diameter of the diffuser body 120 (see, for example, outside sealing surface 344 of FIG. 3F) is in contact with the inner diameter of the housing 110. One or both of these interfacing components may have a taper or other shape which enhances the interference fit of these components, enhancing the seal provided thereby. Further, the seal may be formed where the locator structure interference faces 166 of the housing 110 are in contact with the complementary locator structure interference faces (e.g., faces 324, FIG. 3F) of the diffuser 120. The aggregate length and surface area along which these complementary faces are in contact can enhance the effectiveness of the seal. Moreover, several or all of these sealing interfaces may cooperate or contribute to an effective seal of the housing 110 and the diffuser 120 Where a seal depends on contact between mating or abutting surfaces, the contact may be a tight, friction or interference contact to achieve an effective seal. In addition, a seal may also be achieved using a gasket, sealant, adhesive, chemical weld, thermal weld, ultrasonic weld, or the like, which may be applied or performed at or near the sealing interfaces.

Figure 3A:
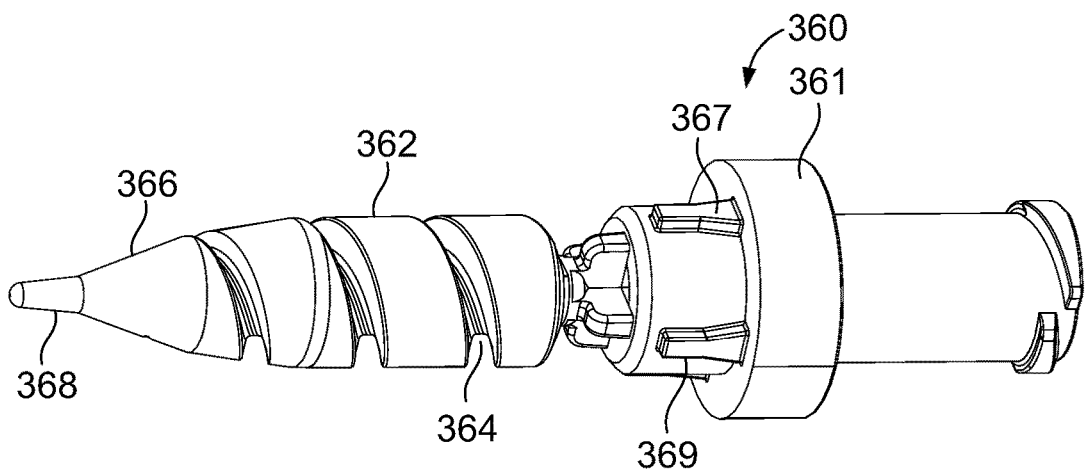
FIG. 3A is a side isometric view of a further alternative example embodiment 360 of a diffuser which may be used in constructing an indicator in accord with an aspect of the invention.
Figure 3B:
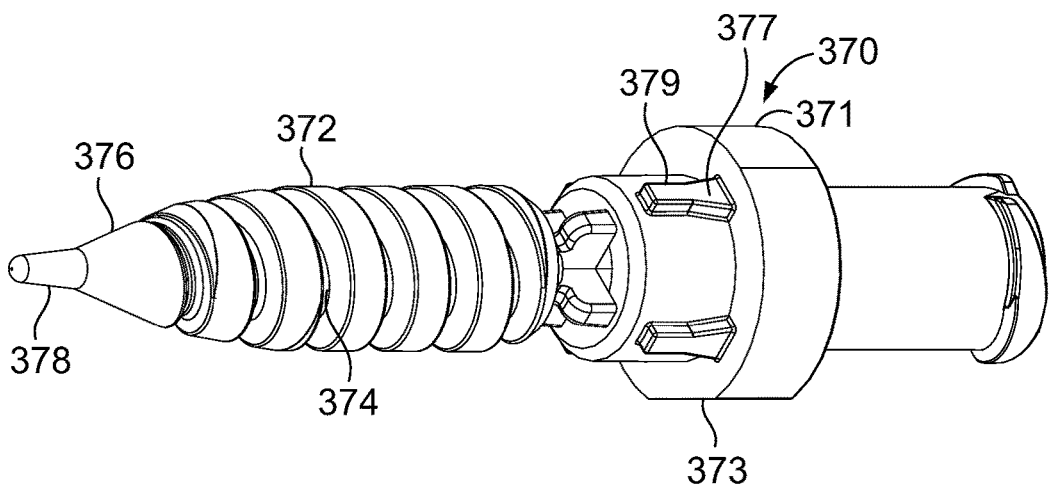
FIG. 3B is a side isometric view of a further alternative example embodiment 370 of a diffuser which may be used in constructing an indicator in accord with an aspect of the invention.
Figure 3C:
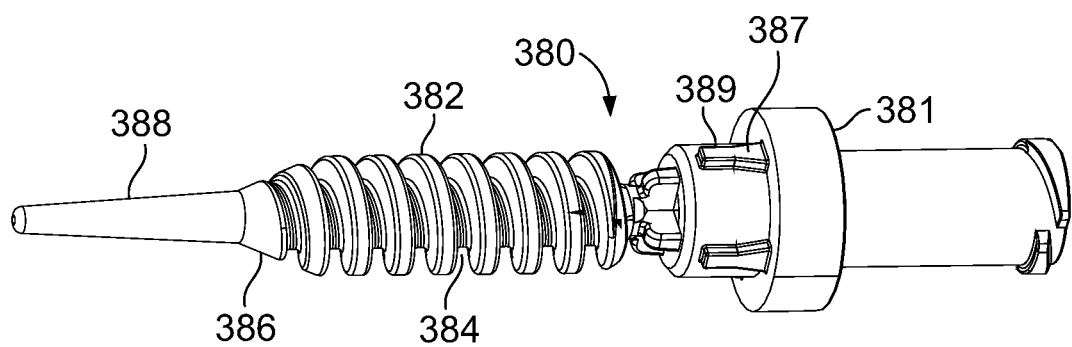
FIG. 3C is a side isometric view of a further alternative example embodiment 380 of a diffuser which may be used in constructing an indicator in accord with an aspect of the invention.
Figure 3D:
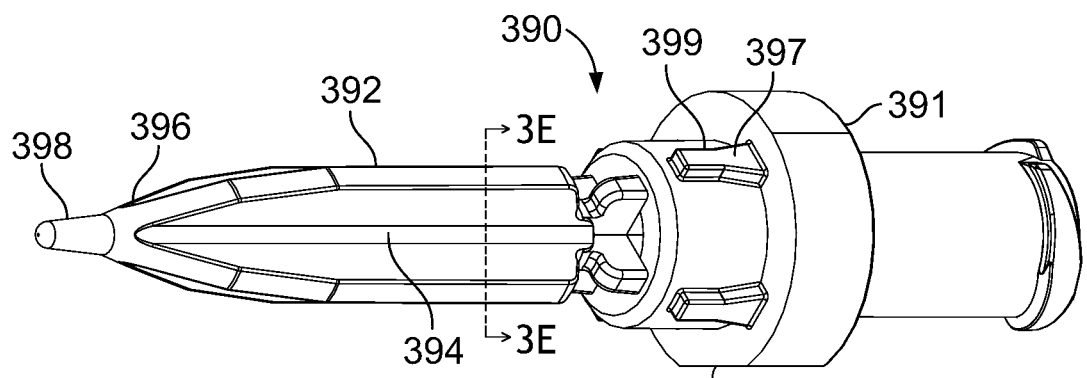
FIG. 3D is a side isometric view of a further alternative example embodiment 390 of a diffuser which may be used in constructing an indicator in accord with an aspect of the invention.
Figure 3E:
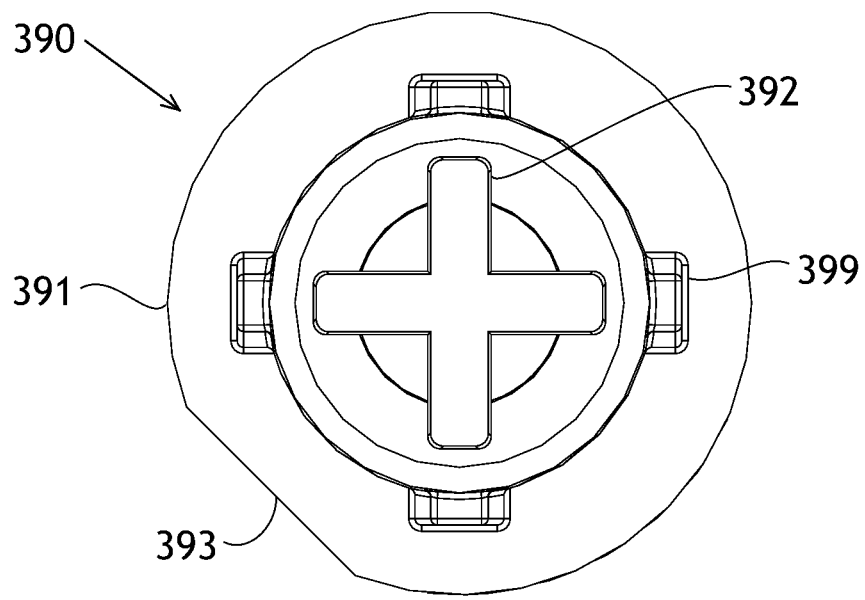
FIG. 3E is a partial cutaway view of the diffuser 390 of FIG. 3D taken along the view lines 3E-3E thereof.
Figure 3F:
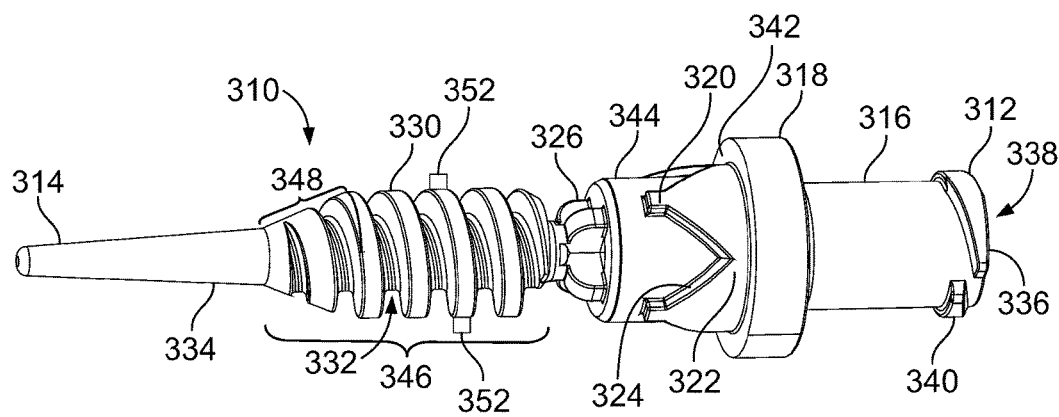
FIG. 3F is a side isometric view of an alternative example embodiment of a diffuser 310 which may be used in constructing an indicator 100 in accord with a further aspect of the invention.

FIG. 3F is a side isometric view of an alternative example embodiment of a diffuser 310 which may be used in constructing an indicator 100 in accord with a further aspect of the invention. Diffuser 310 is generally similar to the diffuser 120 of FIGS. 1C, 1F, and 1G as heretofore described, and except for the differences explained below, the foregoing description of diffuser 120 is applicable to diffuser 310, mutatis mutandis, and is hereby incorporated by reference. Diffuser 310 has a body generally similar to that of diffuser 120. Diffuser 310 has a proximal end 312 and a distal end 314. A connection tube 316 extends from a port 336 at the proximal end 312 and forms a fluid communication chamber, lumen, or passage 338. FIG. 3H is a view looking into the proximal 312 of diffuser 310. In combination, FIGS. 3F and 3H depict some features common to diffuser 120 and diffuser 310 that are not visible in FIGS. 1A-1E, and accordingly, the description of those features here is also applicable to diffuser 120 of FIGS. 1A-1E.

Diffuser 310 has an indicating element section 346, which is attached or connected to the distal extension of connection tube 316 by a channel-forming support 326. A transition section 348 having a tapered diameter provides a transition between the distal end of the indicating element section 346 and a tip section 334 at the distal end of the diffuser body. Between the legs of the support 326, openings or channels 328 allow fluid communication between fluid passage 338 and the volume to the distal side of the connection tube 316. Thus, openings 328 and connection tube 316 provide a fluid communications path 338 between the proximal end port 336 and the remaining volume enclosed by the housing (not shown), which corresponds to the fluid passage thereof. Channel-forming support 326 allows flow through the center of the device. The four chambers at the base allow air and fluid flow during suction and pressure. The four openings 328 allow fluid and air to flow directly in-line with the diffuser to maximize vacuum pressure and fluid flow.

Proximal end 312 preferably has an appropriate fitting 340 for a secure and sealed coupling to a source of vacuum or suction. For example, fitting 340 may be formed as male Luer lock attachment threads on the outer wall of connection tube 316. Any other appropriate coupling or fitting could also be used.

A collar 318 disposed at an intermediate position along connection tube 316 has a diameter larger than that of tube 316 and approximately that of the housing. The collar 318 provides a distal surface 342 against which the proximal end of the housing can bear. In some embodiments, the distal surface 342 and the proximal end of the housing may cooperate to achieve a seal between the housing and the diffuser 310. The collar also serves to retain the reference indicator (not shown in FIGS. 3F and 3H; see reference indicator 116 of FIGS. 1A, 1D, and 1E).

The portion of the connection tube 316 extending distally from the collar 318 has an outside surface 344. When the housing and diffuser 310 are in the assembled configuration, the outside surface 344 and the inside diameter of the housing may be sized, to achieve an interference fit, and may form a seal between the housing and the diffuser 310. The outside surface 344 may also have a taper to enhance its interference fit with the inside diameter of the housing. One or more locator structures 320 are preferably provided on the outside surface 344 of the distal extension of connection tube 316. The locator structure 320 may be formed as structures of increased diameter which cooperate with complementary locator structures on the inner surface near the proximal end of the housing to assist in ensuring that, upon assembly, the diffuser 310 and the occupy desired longitudinal and angular positional relationships with respect to one another. As best seen in FIG. 3F, as part of the locator structure 320, diffuser 310 has a substantially triangular socket 322 for receiving a complementary part of the locator structure of the housing (see locator structure 164, FIG. 1E). The triangular shape of the socket 322 and complementary part on the housing provide a self-aligning capability, such that it is not necessary that the parts be angularly aligned (about the longitudinal axis) prior to assembly. When diffuser and a housing are assembled as an indicator, locator structure interference faces 324 are in contact with the complementary locator structure interference faces 166 (FIG. 1E) of the housing. These contacting faces 324 and 166 may contribute to the seal between the diffuser and the housing. The aggregate length and surface area along which these complementary faces are in contact can enhance the effectiveness of the seal.

The indicating element section 346 has a fluid-channel-forming structure 330 which forms one or more fluid channels 332 and may support an indicating element (not shown in FIG. 3F, but a similar indicating element 108 is shown in FIGS. 1A, 1D, and 1E) in close proximity thereto. In operation, vacuum or suction coupled via port 336 draws fluid into the housing. As best seen in FIG. 3F, the fluid-channel-forming structure 330 and fluid channels 332 have a generally spiral shape in the area of transition section 348 and a generally helical shape in the area of the indicating element section 346. The fluid-channel-forming structure 330 of diffuser 310 has six turns. A different number of turns may be preferred depending on characteristics of the fluid to be tested, such as viscosity and the presence of solids. The presence of the indicating element or the inner wall of the housing substantially prevents the fluid from exiting except through fluid channels 332 and then through openings 328 into connection tube 316. As a result all or nearly all of the fluid flows though fluid channels 332, in contact with or in close proximity to the indicating element. The shape, limited depth, and configuration of the fluid channels 332 forces the fluid in the radial-outward direction. This helps distribute the fluid so as to cause nearly all of the area of the indicating element to be exposed to the fluid as it passes through the fluid channels 332, and this favorable distribution of fluid can occur regardless of the position or orientation of the indicator. This fluid behavior is characteristic of each of the diffusers having spiral or helical fluid channels described herein. If the indicating element is generally pervious to the fluid, the fluid may pass through the indicating element.

In some cases, fluid or air flow through the device, or handling of the device, may tend to dislodge the indicating element from a preferred location with respect to the indicator window or other elements. It is generally desirable that the indicating element not move when the indicator is in use. The fluid-channel-forming structure 330 may have one or more radially-extending tabs 352 to assist in retaining the indicating element in a preferred location. The indicating element retaining tabs 352 may be used on any of the diffusers described herein. The indicating element could also be secured or fixed in location with respect to the diffuser using other structures such as clips or burrs, adhesive attachment, other chemical attachment means, thermal, chemical, or ultrasonic welding, or any other appropriate securement means. Any such indicating element retaining tabs or other means may be used with any of the diffusers disclosed herein.

Figure 3G:
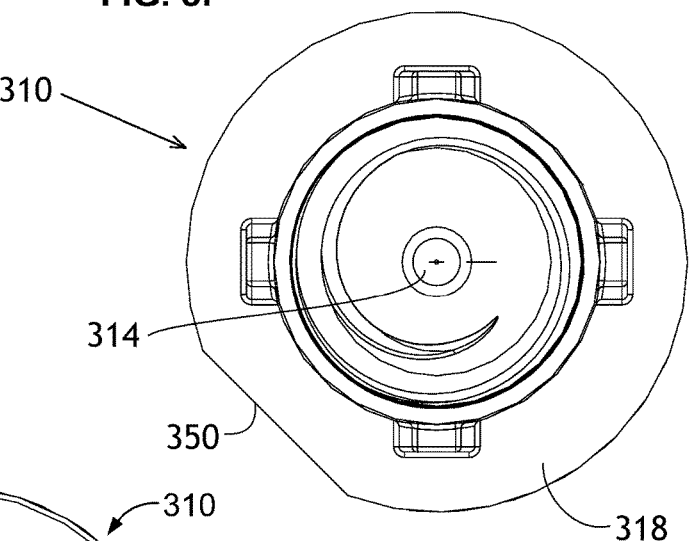
FIG. 3G is an end view of the diffuser 310 of FIG. 3F, taken from the distal end 314 thereof.
Figure 3H:
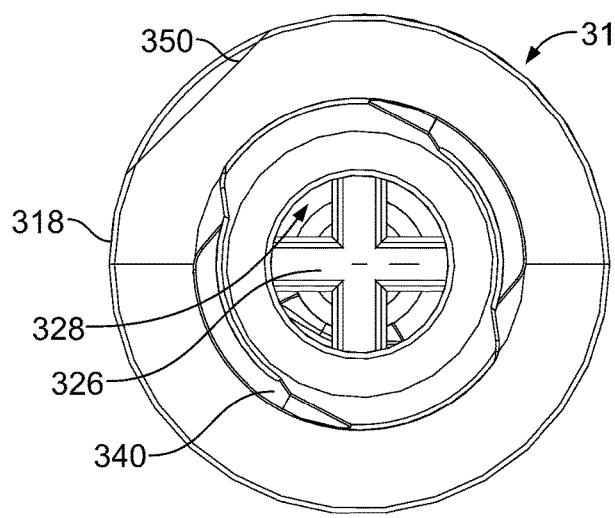
FIG. 3H is an end view of the diffuser 310 of FIGS. 3F and 3G, taken from the proximal end 312 thereof.

As best seen in FIGS. 3G and 3H, collar 318 may have a flat section 350 along a portion of the outer surface, instead of being perfectly round, to provide a key or index that may be used to align the diffuser during assembly or other manufacturing steps. A key or index may also be provided on the housing to align it during assembly or manufacturing.

FIGS. 3A, 3B, 3C, and 3D, are side isometric views of several alternative example embodiments of diffusers which may be used in constructing an indicator 100 in accord with further aspects of the invention. Any of these example embodiments may be used in the indicator 100 in place of the diffuser 120 hereinbefore described.

FIG. 3A is a side isometric view of an embodiment 360 of a diffuser constructed according to a further aspect of the invention. Diffuser 360 is generally similar to the diffuser 120 of FIGS. 1A-1E, and diffuser 310 of FIGS. 3F and 3H, as heretofore described, and except for the differences explained below, the foregoing descriptions of diffusers 120 and 310 are applicable to diffuser 360, mutatis mutandis, and is hereby incorporated by reference.

Diffuser 360 has a body generally similar to that of diffuser 310. A spiral fluid-channel-forming structure 362 forms a fluid channel 364, similar to fluid-channel-forming structure 330 and fluid channels 332 of diffuser 310. The fluid-channel-forming structure 362 and fluid channel 364 have three turns instead of six. A conical transition region 366 joins the fluid-channel-forming structure 362 to a tip section 368, which is shorter than the tip section of diffuser 310. Locator structures 369, similar in function to the locator structures 320 of diffuser 310, are formed as generally rectangular tabs with trapezoidal enlargements near their proximal ends 367 adjacent collar 361. A corresponding modification to a housing would be required to accommodate the difference in the shape of the diffuser from that of the diffusers 120 and 310.

FIG. 3B is a side isometric view of an embodiment 370 of a diffuser constructed according to a further aspect of the invention. Diffuser 370 is generally similar to the diffuser 120 of FIGS. 1A-1E, and diffuser 310 of FIGS. 3F and 3H, as heretofore described, and except for the differences explained below, the foregoing descriptions of diffusers 120 and 310 are applicable to diffuser 370, mutatis mutandis, and is hereby incorporated by reference.

Diffuser 370 has a body generally similar to that of diffuser 310. A spiral fluid-channel-forming structure 372 forms a fluid channel 374, similar to fluid-channel-forming structure 330 and fluid channels 332 of diffuser 310. The fluid-channel-forming structure 372 and fluid channel 374 have six turns. A conical transition region 376 joins the fluid-channel-forming structure 372 to a tip section 378, which is shorter than the tip section of diffuser 310. Locator structures 379, similar in function to the locator structures 320 of diffuser 310, are formed as generally rectangular tabs with trapezoidal enlargements near their proximal ends 377 adjacent collar 371. A corresponding modification to a housing would be required to accommodate the difference in the shape of the diffuser from that of the diffusers 120 and 310. A flat section 373 on the outer surface of collar 371 provides a key or index that may be used to align the diffuser 370 during assembly or other manufacturing steps.

FIG. 3C is a side isometric view of an embodiment 380 of a diffuser constructed according to a further aspect of the invention. Diffuser 380 is generally similar to the diffuser 120 of FIGS. 1A-1E, and diffuser 310 of FIGS. 3F and 3H, as heretofore described, and except for the differences explained below, the foregoing descriptions of diffusers 120 and 310 are applicable to diffuser 380, mutatis mutandis, and is hereby incorporated by reference.

Diffuser 380 has a body generally similar to that of diffuser 310. A spiral fluid-channel-forming structure 382 forms a fluid channel 384, similar to fluid-channel-forming structure 330 and fluid channels 332 of diffuser 310. The fluid-channel-forming structure 382 and fluid channel 384 have nine turns instead of six. A spiral transition region 386 joins the fluid-channel-forming structure 382 to a tip section 388 which is similar to the tip section 334 of diffuser 310. Locator structures 389, similar in function to the locator structures 320 of diffuser 310, are formed as generally rectangular tabs with trapezoidal enlargements near their proximal ends 387 adjacent collar 381.

FIG. 3D is a side isometric view of an embodiment 390 of a diffuser constructed according to a further aspect of the invention. FIG. 3E is a partial cutaway view of the diffuser 390 taken along the view lines 3E-3E of FIG. 3D. Diffuser 390 is generally similar to the diffuser 120 of FIGS. 1A-1E, and diffuser 310 of FIGS. 3F and 3H, as heretofore described, and except for the differences explained below, the foregoing descriptions of diffusers 120 and 310 are applicable to diffuser 390, mutatis mutandis, and is hereby incorporated by reference.

Diffuser 390 has a body generally similar to that of diffuser 310. A star- or cross-shaped fluid-channel-forming structure 392 forms a fluid channel 394, similar to fluid-channel-forming structure 140 and fluid channels 154 of diffuser 120. A tapered transition region 396 joins the fluid-channel-forming structure 392 to a tip section 398, which is shorter than the tip section of diffuser 120. Locator structures 399, similar in function to the locator structures 320 of diffuser 310, are formed as generally rectangular tabs with trapezoidal enlargements near their proximal ends 397 adjacent collar 391. A corresponding modification to a housing would be required to accommodate the difference in the shape of the diffuser from that of the diffusers 120 and 310. A flat section 393 on the outer surface of collar 391 provides a key or index that may be used to align the diffuser 390 during assembly or other manufacturing steps.

FIGS. 4A, 4B, 5A, 5B, 5C, 5E, 6A, 6B, 6C, 6D, 6E, and 6F depict several example embodiments, according to further aspects of the invention, of apparatus for obtaining and containing a fluid obtained from a person or animal, measuring or detecting one or more characteristics of the fluid, and displaying an indication relating to the measurement. The embodiments of FIGS. 4A, 4B, 5A, 5B, 5C, 5E, 6A, 6B, 6C, 6D, 6E, and 6F, the "low-volume embodiments", are generally similar to the earlier described embodiments of 1A-1E, 2A-2F, and 3A-3H, but encompass modifications from those earlier described that render the embodiments more suitable for use when a very limited volume of fluid is available to be tested. These latter embodiments may be appropriate for use with neonatal patients, veterinary patients, and other similar instances in which the patient is small or limited fluid is available to be tested.

In the discussion of the low-volume embodiments below, newly-introduced example embodiments may be described with reference to similarity with an earlier-described example embodiment. In each case, the foregoing description of the corresponding referenced embodiment is hereby incorporated by reference, and the newly-introduced embodiment shall be considered to have structures, features, components, and functions similar to or equivalent to the referenced embodiment, mutatis mutandis, except for: (1) items specifically identified as different in the description; and (2) the following general low-volume modification. Each of the newly-introduced embodiments is modified from the referenced embodiment in that its size is reduced, and the volumes of fluid-transfer passages, conduits, chambers, lumina, and other interstitial spaces which fluid under test may occupy, are reduced or minimized. In addition to the reducing the volume of fluid needed to accomplish a measurement, this modification also reduces both the amount of distance the fluid must travel to reach and saturate the indicating element, and the elapsed time of such travel (compared to those required in connection with the earlier-described indicators).

Figure 4A:
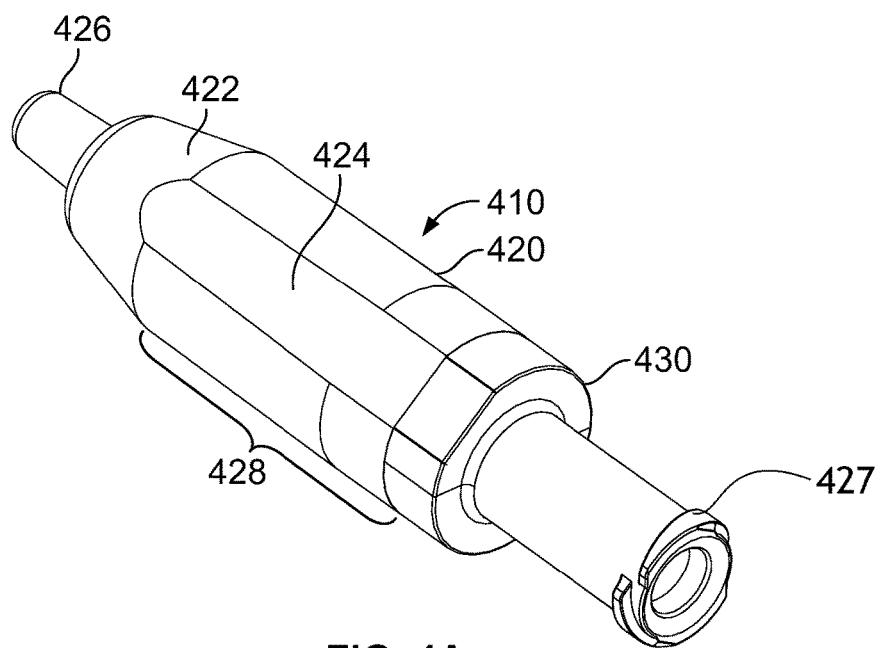
FIG. 4A is an isometric view of a further example embodiment 410 of an indicator device constructed according to an aspect of the invention.
Figure 4B:
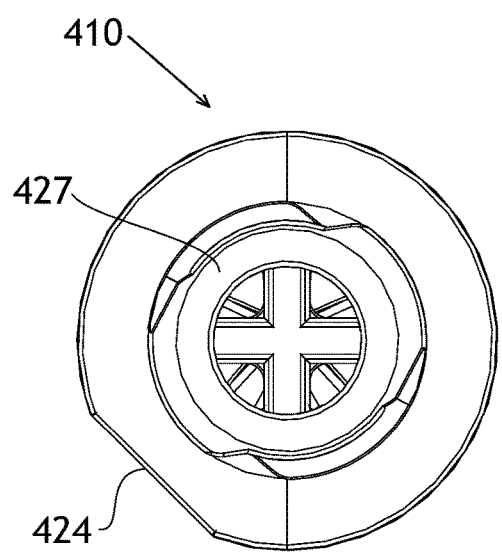
FIG. 4B is an end view of the indicator 410 of FIG. 4A, looking toward the proximal end 427 thereof.
Figure 4C:
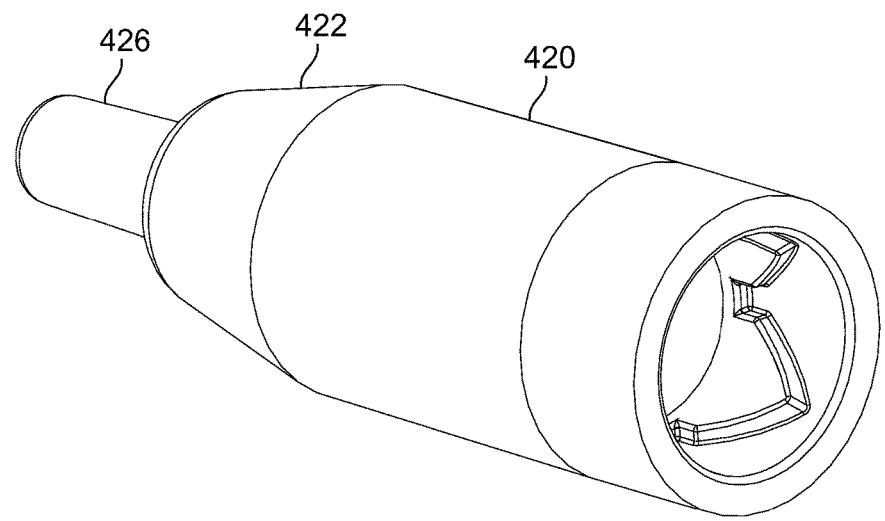
FIG. 4C is a side isometric view of the indicator 410 of FIGS. 4A-4B.

FIG. 4A is an isometric view of an embodiment 410 of an indicator device constructed according to an aspect of the invention, which is generally similar to the indicator 100 of FIGS. 1A-1E, subject to the low-volume modification. Indicator 410 comprises a housing 420 and a diffuser 430, which are respectively similar to housing 110 and diffuser 120 of FIGS. 1A-1E, subject to the low-volume modification. The proximal end is shown at 427. FIG. 4B is an end view of the indicator 410 of FIG. 4A, looking toward the proximal end 427 thereof; FIG. 4C is a side isometric view of the housing 420. A flat section 424 on the outer surfaces of both housing 420 and diffuser 430 provides a keys or indices that may be used to align the housing 420 and diffuser 430 during assembly or other manufacturing steps. The housing 420 has a main body section 428 and a thin distal tip 426 for receiving fluid from a fluid transport source (not shown), which may take the form of tubing, conduits, adapters, appliances, containers, reservoirs, catheters, feeding tubes, suction tubes, or the like, which may be used in a clinical environment to furnish the fluid with which indicator 410 is to be used to perform a test, or obtain a measurement, or indication of one or more characteristic or property of the fluid. The distal tip 426 may have a diameter and be formed with a "catheter tip" shape suitable for mating, coupling, or connection with a catheter, such as a nasogastric tube or feeding tube which is inserted into a patient's stomach and which serves as the fluid transport source. Further, the size and shape of distal tip 426 may be selected to be suitable for use with the types of tubes, catheters, or other fluid transport source that are used to treat neo-natal or other very small patients. The catheter tip can also be mated with other types of receiving connector, plugs, hubs, and the like. A distal transition section 422 provides the transition between the main body section 428 and the distal tip 426. The shape of the distal transition section 422 differs from the shape of the housings 110 and 190 of FIGS. 1A-1E, 2B, 2C, and 2F in that the distal transition section 422 has a snubbed, relatively sharp taper, instead of an elongated gradual taper. The shape of distal transition section 422 is selected to minimize the internal volume so as to maximize the amount of available fluid that is routed to the indicating element. In addition to the reducing the volume of fluid needed to accomplish a measurement, this feature also reduces both the amount of distance the fluid must travel to reach and saturate the indicating element, and the elapsed time of such travel (compared to those required in connection with the earlier-described indicators).

Figure 5A:
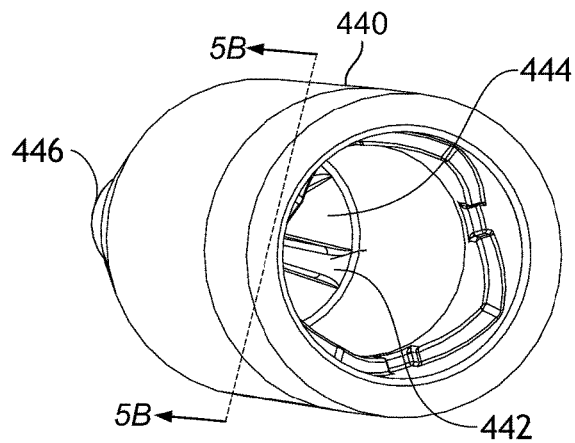
FIG. 5A is a view of a further example embodiment 440, constructed according to an aspect of the present invention, of a housing which is similar to the housing 420 of FIGS. 4A and 5C, but which provides a central fluid passage modified cross section to incorporate fluid guide channels.
Figure 5B:
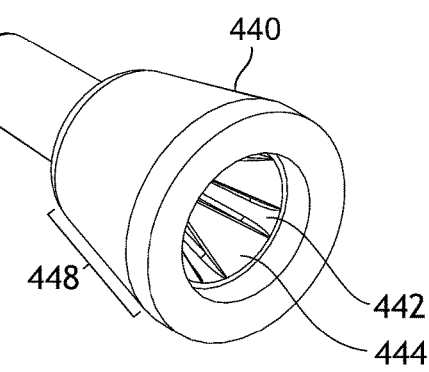
FIG. 5B is a cutaway view of the housing 440 of FIG. 5A taken along the view lines 5B-5B, looking into the housing from its proximal end.
Figure 5C:
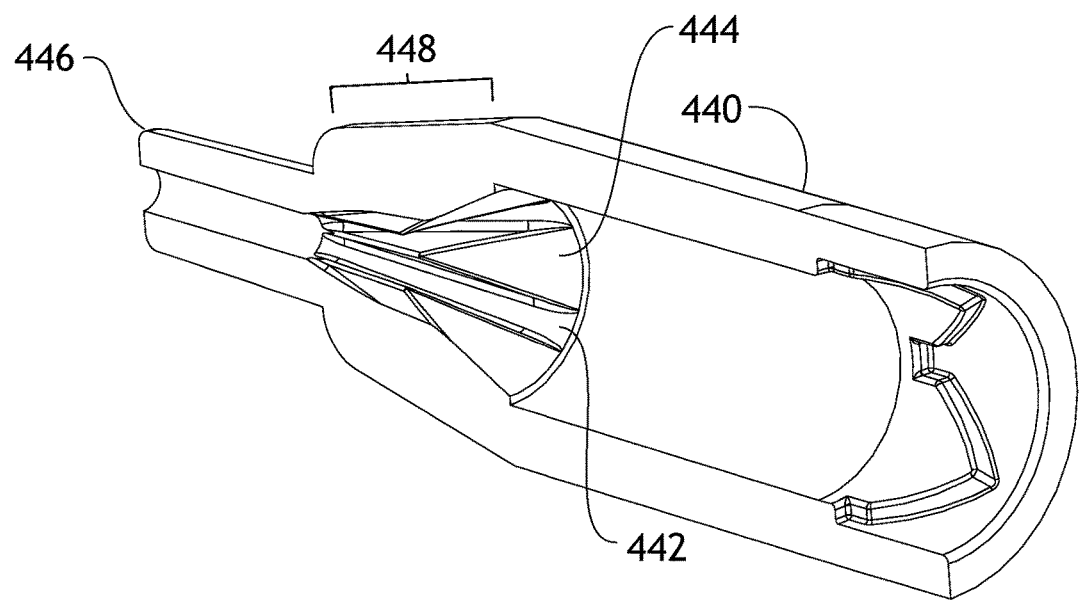
FIG. 5C is a is a partial cutaway view of the housing 440 of FIGS. 5A-5B.
Figure 5D:
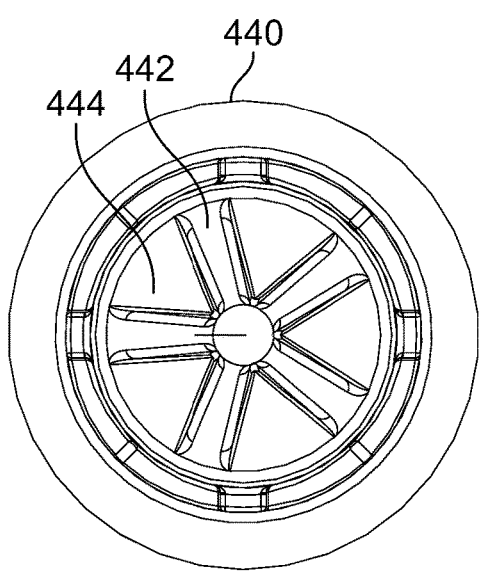
FIG. 5D is an end view looking into the housing 440 of FIGS. 5A-5C from the proximal end thereof.
Figure 5E:
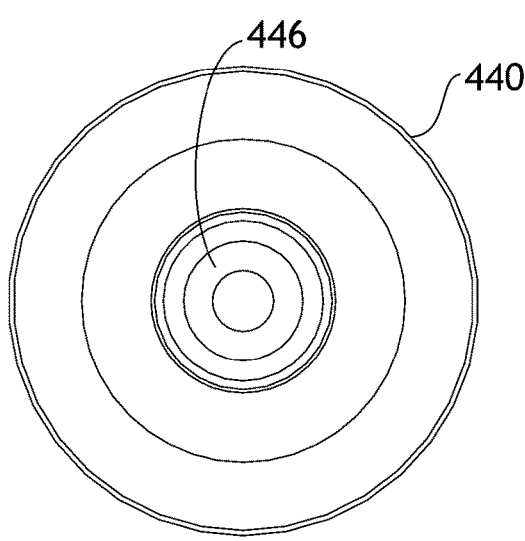
FIG. 5E is an end view of the housing 440 of FIGS. 5A-5D looking toward the distal end 446 thereof.

FIG. 5A is view of a further example embodiment of a housing 440, constructed according to an aspect of the present invention, of a housing which is similar to the housing 420 of FIGS. 4A-4C, but which provides a central fluid passage modified cross section to incorporate fluid guide channels 442 on the interior surface 444 of distal transition section 448. Housing 440 is further similar to housing 190 of FIGS. 2B-2F, subject to the low-volume modification. FIG. 5B is a cutaway view of the housing 440 of FIG. 5A taken along the view lines 5B-5B. FIG. 5C is a is a partial cutaway view of the housing 440 of FIGS. 5A-5B. FIG. 5D is an end view looking into the housing 440 of FIGS. 5A-5C from the proximal end thereof. FIG. 5E is an end view of the housing 440 of FIGS. 5A-5D looking toward the distal end 446 thereof.

Figure 6A:
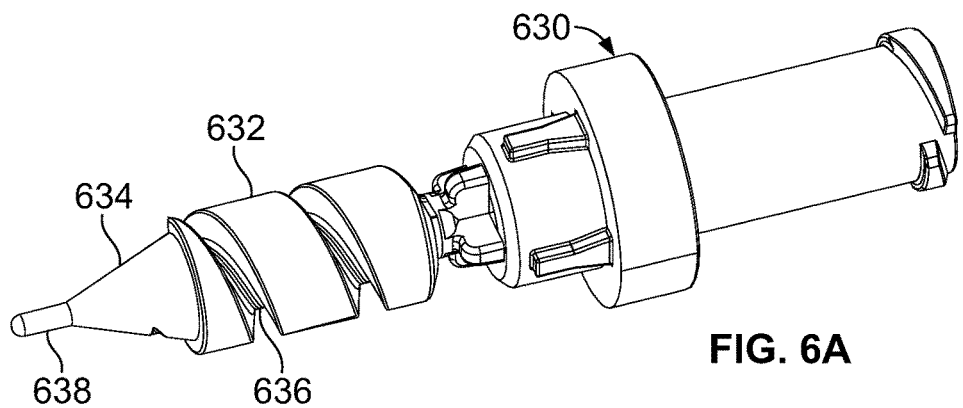
FIG. 6A is a side view of a further example embodiment 630, according to an aspect of the invention, of a diffuser exhibiting a modification to accommodate lower fluid volume than earlier-described embodiments.
Figure 6B:
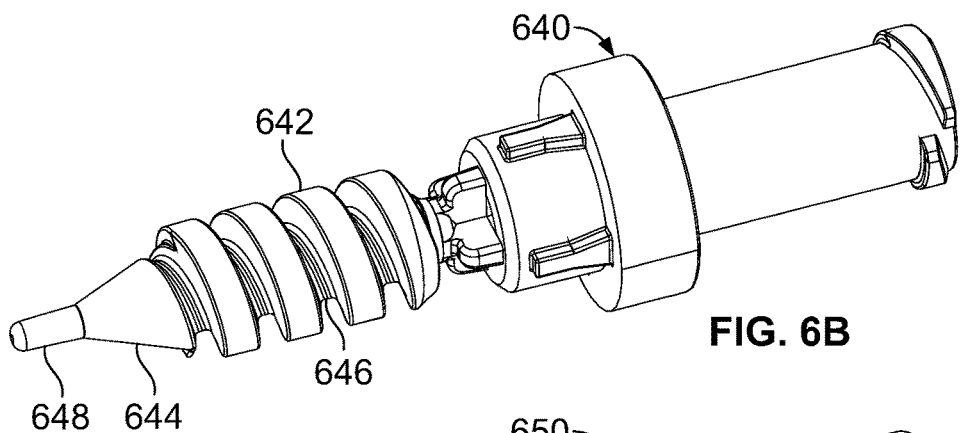
FIG. 6B is a side view of a further example embodiment 640, according to an aspect of the invention, of a diffuser exhibiting a modification to accommodate lower fluid volume than earlier-described embodiments.
Figure 6C:
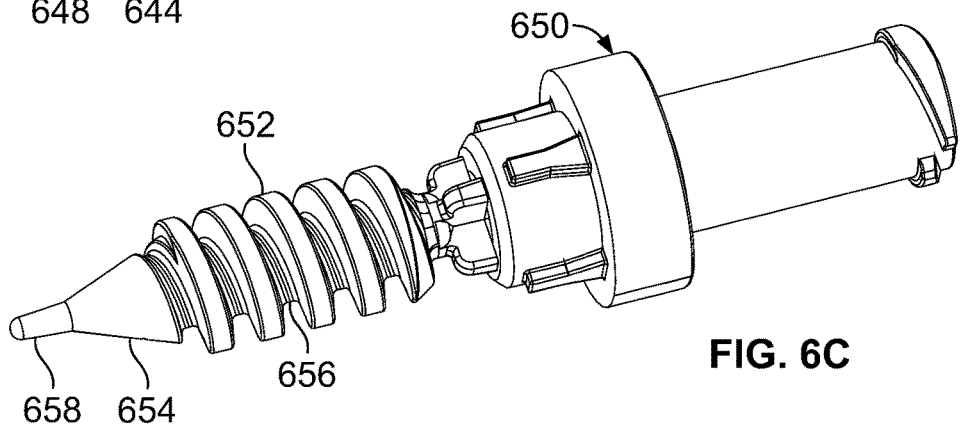
FIG. 6C is a side view of a further example embodiment 650, according to an aspect of the invention, of a diffuser exhibiting a modification to accommodate lower fluid volume than earlier-described embodiments.
Figure 6D:
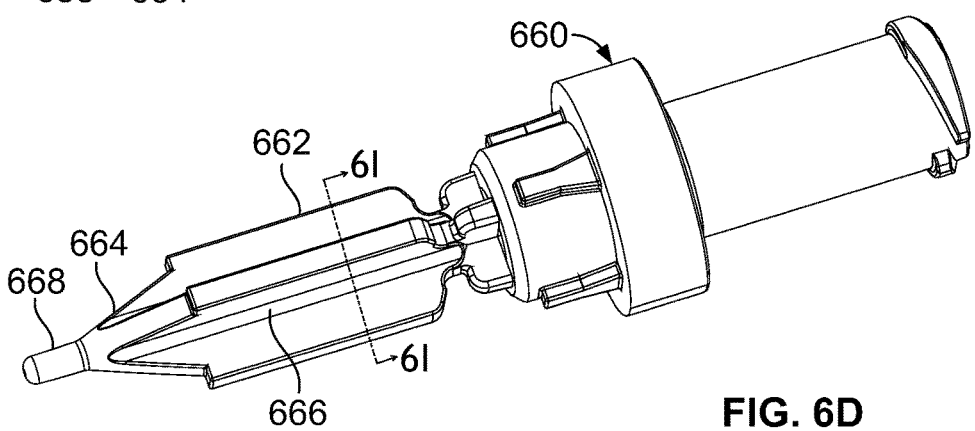
FIG. 6D is a side view of a further example embodiment 660, according to an aspect of the invention, of a diffuser exhibiting a modification to accommodate lower fluid volume than earlier-described embodiments.
Figure 6F:
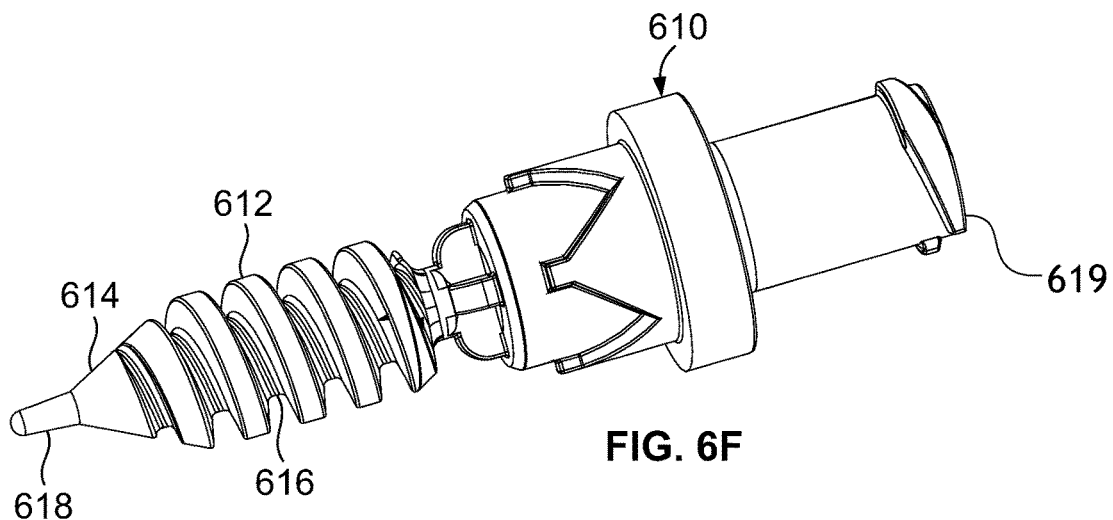
FIG. 6F is an isometric view of a further example embodiment 610 of a diffuser, according to an aspect of the invention, exhibiting a lower-fluid-volume modification.
Figure 6G:
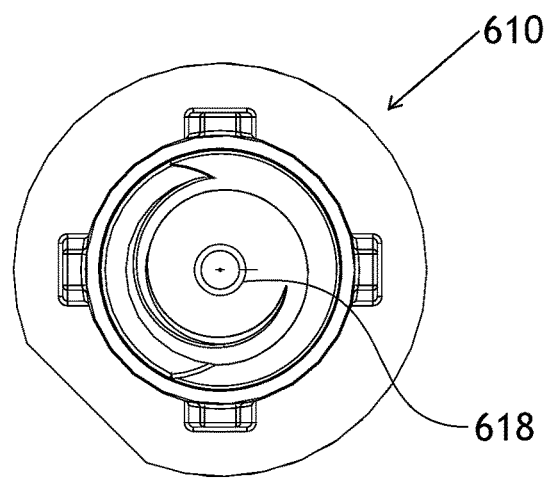
FIG. 6G is an end view of the diffuser 610 of FIG. 6F, looking toward the distal end 618 thereof.
Figure 6H:
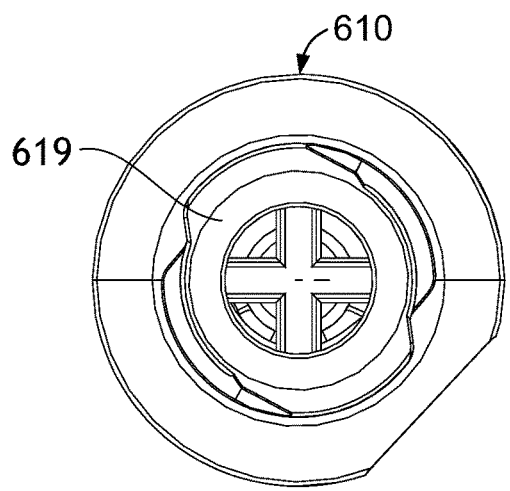
FIG. 6H is an end view of the diffuser 610 of FIGS. 6F-6G, looking toward the proximal end 619 thereof.

FIG. 6F is a view of a further example embodiment 610, constructed according to an aspect of the present invention, of a diffuser which is similar to the diffuser 310 of FIGS. 3F-3H, subject to the low-volume modification. Diffuser 610 has a fluid-channel-forming structure 612 and a fluid channel 616 formed thereby. The proximal end is shown by 619. The fluid-channel-forming structure 612 and fluid channel 616 are in a spiral configuration and have five turns. Diffuser 610 further has a sharp-tapered transition section 614 and a shorter distal tip 618, which accommodates a smaller housing that more efficiently routes available fluid to the indicating element.

FIG. 6A is a side view of a further example embodiment 630, constructed according to an aspect of the present invention, of a diffuser which is similar to the diffuser 360 of FIG. 3A, exhibiting a modification to accommodate lower fluid volume than earlier-described embodiments. Diffuser 630 has a fluid-channel-forming structure 632 and a fluid channel 636 formed thereby. The fluid-channel-forming structure 632 and fluid channel 636 are in a spiral configuration and have two turns. Diffuser 630 further has a sharp-tapered transition section 634 and a shorter distal tip 638, which accommodates a smaller housing that more efficiently routes available fluid to the indicating element.

FIG. 6B is a view of a further example embodiment 640, constructed according to an aspect of the present invention, of a diffuser which is similar to the diffuser 360 of FIG. 3A, exhibiting a lower-fluid-volume modification. Diffuser 640 has a fluid-channel-forming structure 642 and a fluid channel 646 formed thereby. The fluid-channel-forming structure 642 and fluid channel 646 are in a spiral configuration and have four turns. Diffuser 640 further has a sharp-tapered transition section 644 and a shorter distal tip 648, which accommodates a smaller housing that more efficiently routes available fluid to the indicating element.

FIG. 6C is a view of a further example embodiment 650, constructed according to an aspect of the present invention, of a diffuser which is similar to the diffuser 360 of FIG. 3A, exhibiting a lower-fluid-volume modification. Diffuser 650 has a fluid-channel-forming structure 652 and a fluid channel 656 formed thereby. The fluid-channel-forming structure 652 and fluid channel 656 are in a spiral configuration and have five turns. Diffuser 650 further has a sharp-tapered transition section 654 and a shorter distal tip 658, which accommodates a smaller housing that more efficiently routes available fluid to the indicating element.

Figure 6I:
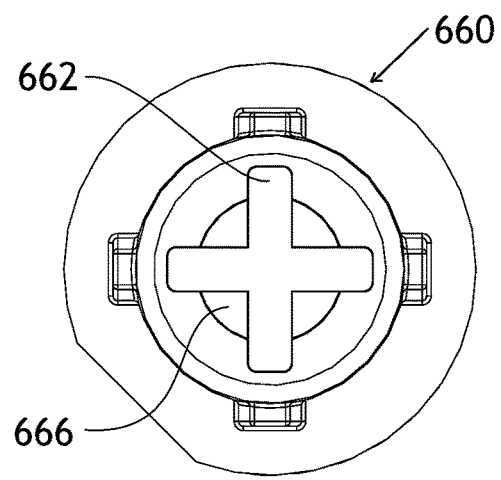
FIG. 6I is an end view of the diffuser 660 of FIG. 6D, taken along the view lines 6I-6I thereof, looking toward the distal end 668 thereof.

FIG. 6D is a view of a further embodiment 660, constructed according to the present invention, of a diffuser which is similar to the diffuser 390 of FIG. 3D, exhibiting a lower-fluid-volume modification. FIG. 6I is an end view of the diffuser 660 of FIG. 6D, taken along the view lines 6I-6I thereof, looking toward the distal end 668 thereof. Diffuser 660 has a fluid-channel-forming structure 662 and fluid channels 666 formed thereby. The fluid-channel-forming structure 662 has a star- or cross-shaped cross-section forming longitudinally-extending parallel fluid channels 666. Diffuser 660 further has a sharp-tapered transition section 664 and a shorter distal tip 668, which accommodates a smaller housing that more efficiently routes available fluid to the indicating element.

Figure 1F:
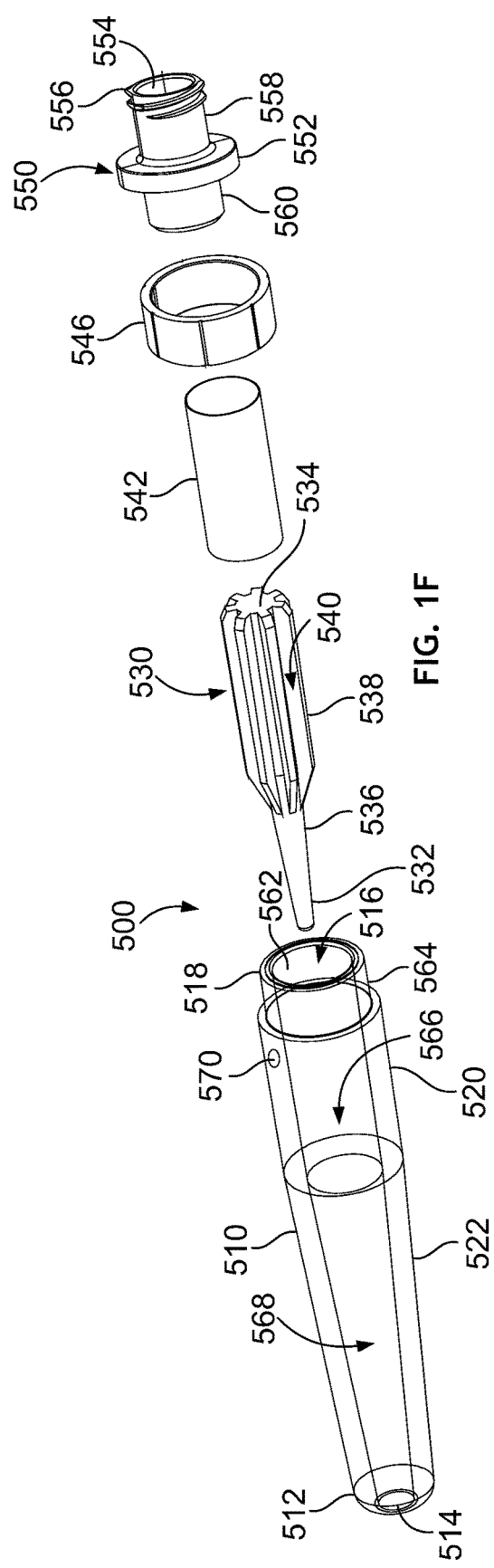
FIG. 1F is a partial exploded view of further example embodiment 500 of a body fluid characteristic indicator, according to a further aspect of the invention.

FIG. 1F is a partial exploded view of another example embodiment 500, according to a further aspect of the invention, of apparatus for obtaining and containing a fluid obtained from a person or animal, measuring or detecting one or more characteristics of the fluid, and displaying an indication relating to the measurement. Indicator 500 is generally similar to the indicator 100 of FIGS. 1A-1E, but the functions of controlling/routing the flow of fluid into contact with the indicating element are provided by plural individual components rather than a single, integrated diffuser element. Except for the differences explained hereinbelow, the foregoing description of indicator 100 is applicable to indicator 500, mutatis mutandis, and is hereby incorporated by reference.

Indicator 500 has a housing 510, a diffuser element 530 contained in the housing, and a proximal end cap 550 that closes and seals the housing. The housing 510 has a generally tubular body 568 with a distal end 512 and a proximal end 518. The distal end 512 has an intake port or opening 514. The proximal end 518 has a proximal end opening 516. A central fluid communication chamber, lumen, or passage 566 extends between distal end port 514 and housing proximal end opening 516. The housing body 568 has, adjoined in series from the distal end 512 to the proximal end 518 a tapered main section 522, indicator window section 520, and a race section of slightly reduced diameter to accommodate a rotatable reference indicator or wheel.

A diffuser 530 is disposed within the interior of body 568 in the fluid passage 566. The diffuser has a distal end 532, a tip section 536 and a proximal end 534. Between the tip section 536 and the proximal end 534 are one or more fluid-channel-forming structures 538, which, in combination with any central body portion of the diffuser 530, the body 568, and the indicating element 542 form one or more fluid channels 540. Although the diffuser 530 of FIG. 1F is depicted as having a star-shaped cross section, other diffuser geometries could also be used. For example, the geometries of the fluid-channel-forming structures of any of diffusers 330, 360, 370, 380, 390 could be used, with appropriate modifications to accommodate the differences in the shape of the housing and the connection to proximal end cap 550.

The indicating element 542 may be formed as a tube or roll and be disposed coaxially with the diffuser. The reference indicator 546 is preferably disposed coaxially around the body 568 at the reference indicator race 564. The reference indicator 546 preferably has a inside diameter smaller than the outside diameter of the body 568 at the indicator window section 520 but larger than the diameter of the reference indicator race 564, so that the reference indicator 546 may be retained between the indicator window section 520 and a collar 552 of the proximal end cap 550. Preferably, the reference indicator 546 may be rotated by the user.

The proximal end cap 550 acts as a closure and seal for the housing 510 and provides a proximal end or outflow port 554 in fluid communication with the housing fluid passage 566. The proximal end cap 550 has a connection tube 558 extending from proximal end port 554 through collar 552. The connection tube 558 has a portion extending distally of the collar 552. The closure and seal may be achieved by a tight friction or interference fit between the housing inner wall surface 562 and the outer surface of the connection tube extension 560. The seal may also be achieved using a gasket, sealant, adhesive, chemical weld, thermal weld, ultrasonic weld, or the like, which may be applied or performed at or near the sealing interfaces. A Luer lock fitting 556 may be provided on the proximal end port 554 to facilitate connection to a source of vacuum or suction.

A port 570 may be provided on a portion of the housing 510 to allow fluid to be withdrawn, e.g., for other testing, examination, treatment, diagnosis, or procedures. The port 570 also allows reagents, dies, other chemicals, or other material to be added. This could be used, for example, where the indicator may furnish a measurement only with the added material, or where the indicator may furnish an additional useful measurement, or additional precision in measurement, after the added material. The port 570 may be by a puncturable seal, so that material may be added or removed via a needle and syringe or the like, and the seal may be a self-reclosing seal to avoid leakage in or out through the port after use.

The indicator 500 may operate in the same way as indicator 100 of FIGS. 1A-1E.

Figure 7A:
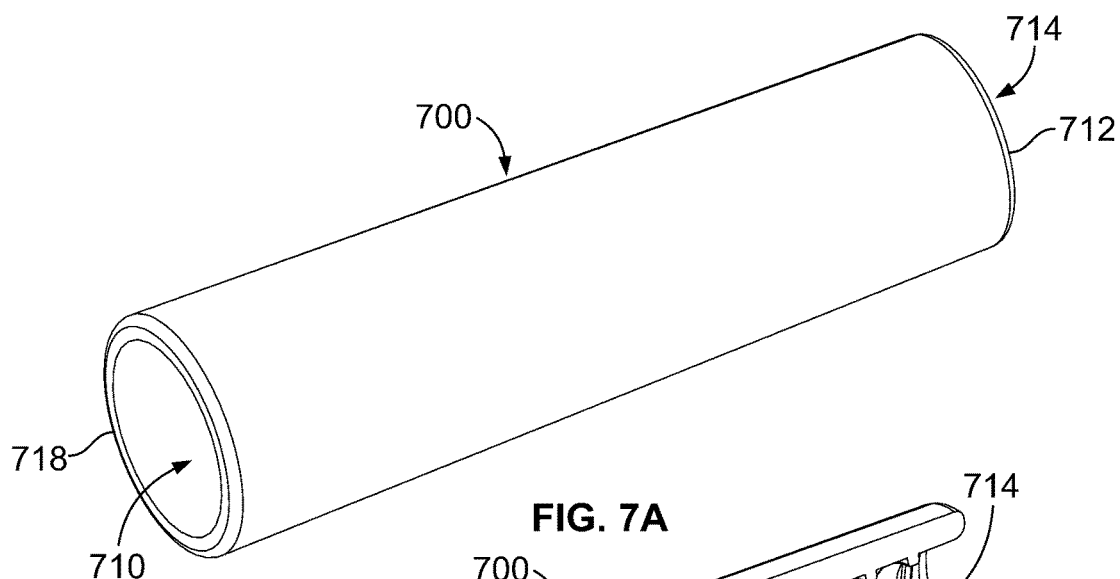
FIG. 7A is a side view of an adapter 700 constructed according to an aspect of the present invention for converting from a catheter tip connection to a locking or threaded fitting such as a Luer lock fitting.
Figure 7B:
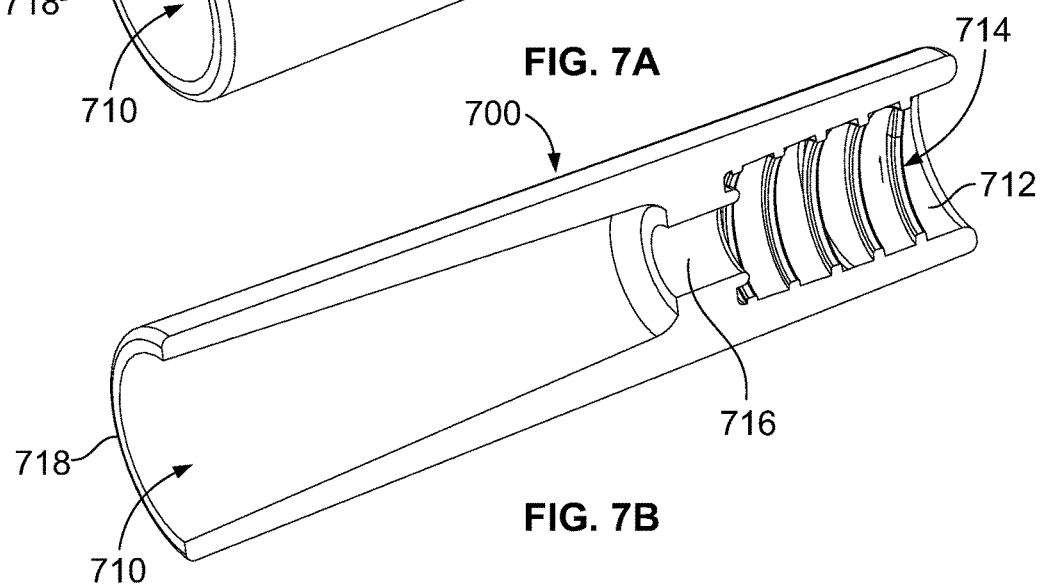
FIG. 7B is a cutaway view of the adapter 700 of FIG. 7A.
Figure 7C:
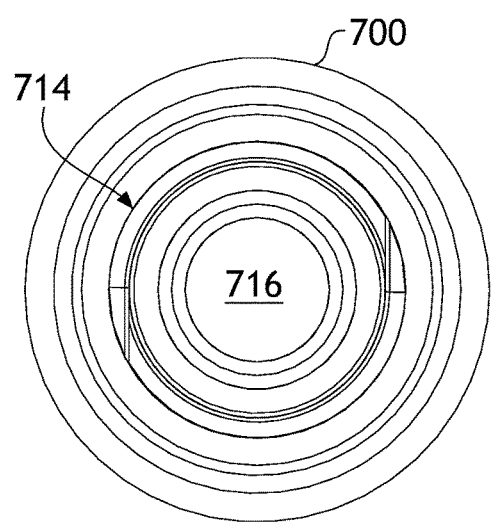
FIG. 7C is an end view of the adaptor 700 of FIGS. 7A-7B looking toward the proximal end 712 thereof.
Figure 7D:
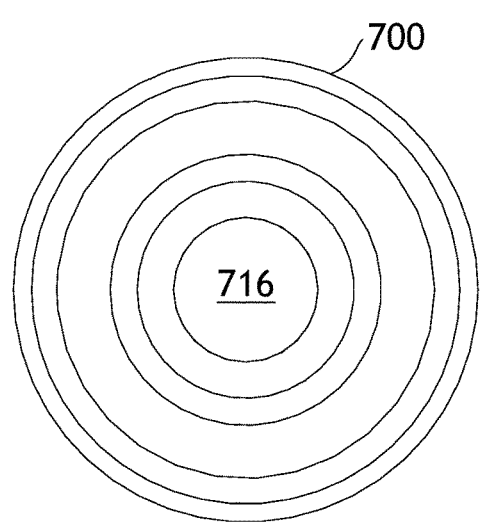
FIG. 7D is an end view of the adaptor 700 of FIGS. 7A-7C looking toward the distal end 718 thereof.
Figure 7E:
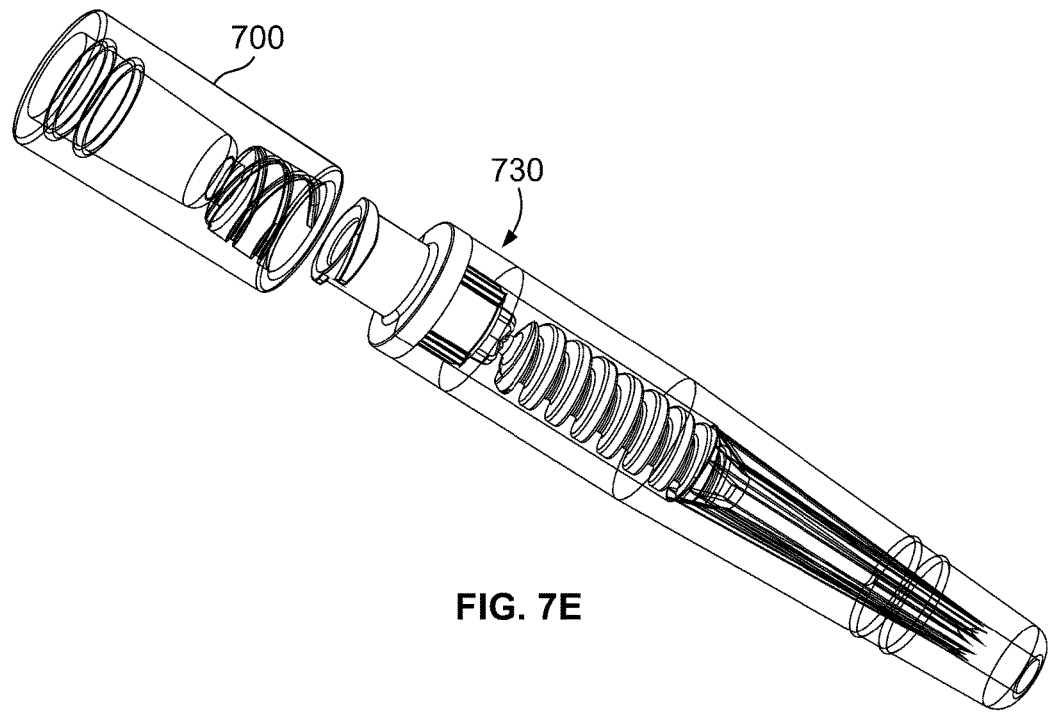
FIG. 7E is a side stylized transparent view of the adaptor 700 of FIGS. 7A-7D as it may be used with an example embodiment 730 of an indicator according to an aspect of the invention, prior to assembly of the adaptor 700 on the indicator 730.
Figure 7F:
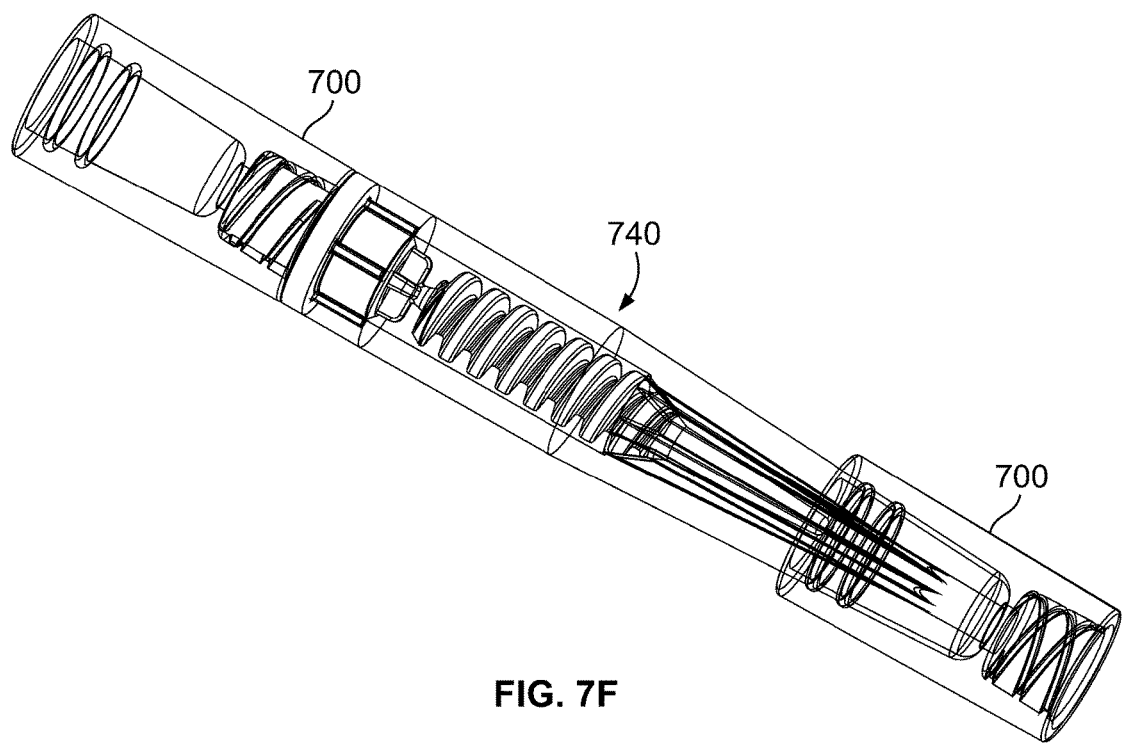
FIG. 7F is a side stylized transparent view of two instances of the adaptor 700 of FIGS. 7A-7D as they may be assembled onto each end of an example embodiment 740 of an indicator according to an aspect of the invention.
Figure 7G:
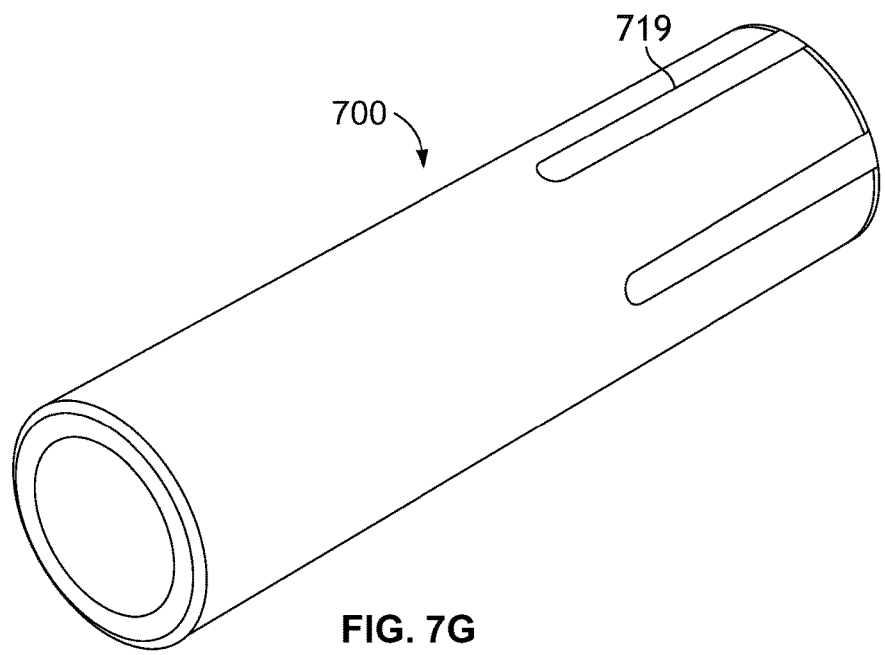
FIG. 7G is a side view of the adaptor 700 showing striations 719 which may optionally be applied thereto.

FIG. 7A is a side view of an adapter 700 constructed according to an aspect of the present invention for converting from a catheter tip connection to a locking or threaded fitting such as a Luer lock fitting. FIG. 7B is a cutaway view of the adapter 700 of FIG. 7A. As best seen in FIG. 7B, the adapter 700 has a proximal end 718 with a female catheter tip socket or receptacle 710 and a proximal end 712 with a female threaded locking fitting 714, such as a Luer lock fitting. A fluid passage 716 allows fluid communication between the receptacle 710 and the fitting 714. FIG. 7C is an end view of the adaptor 700 of FIGS. 7A-7B looking toward the proximal end 712 thereof. FIG. 7D is an end view of the adaptor 700 of FIGS. 7A-7C looking toward the distal end 718 thereof. FIG. 7G is a side view of the adaptor 700 showing striations 719 which may optionally be applied thereto. Striations 719 may optionally be applied to the outer wall of the adapter 700 to improve the strength of the wall and to provide a stable gripping surface when threading the adapter onto a mating fitting. FIG. 7E is a side stylized transparent view of the adaptor 700 of FIGS. 7A-7D as it may be used with an example embodiment 730 of an indicator according to an aspect of the invention, prior to assembly of the adaptor 700 on the indicator 730. FIG. 7F is a side stylized transparent view of two instances of the adaptor 700 of FIGS. 7A-7D as they may be assembled onto each end of an example embodiment 740 of an indicator according to an aspect of the invention. As best seen in FIGS. 7E and 7F, the adapter 700 may be used, for example, with an indicator 100, or any similar indicator 730 or 740, adapt the Luer lock fitting (such as Luer lock fitting 134 of FIGS. 1C, 1F, and 1G) on the proximal end to a catheter tip connection. The adapter 700 may also be used, for example, to adapt the catheter tip connection on the distal end 102 to a Luer lock fitting. As best seen in FIG. 7F, two adapters could be used on the same indicator. The adapter could also be used with other devices. The adapter provides a sufficiently good seal to accommodate the pressure or vacuum/suction encountered in a clinical environment.

Figure 8A:
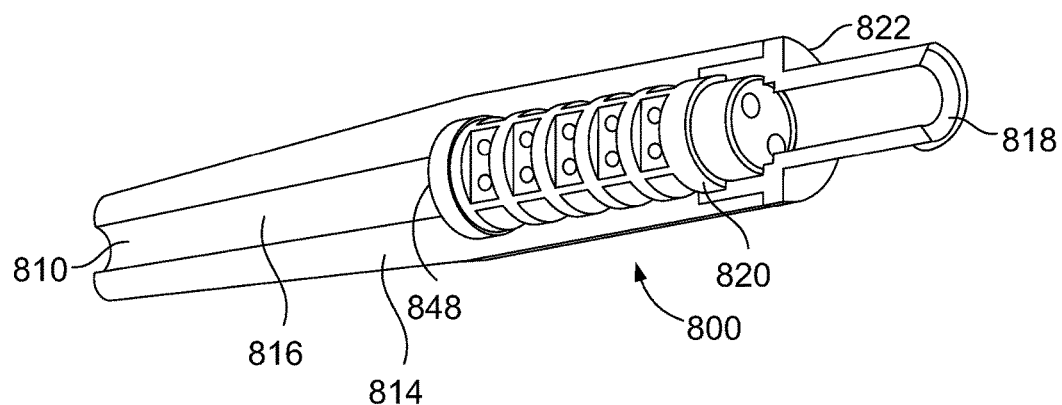
FIG. 8A is a partial cutaway view of another example embodiment 800 of an indicator constructed according to a further aspect of the invention.

FIG. 8A is a partial cutaway view of another example embodiment 800, according to a further aspect of the invention, of apparatus for obtaining and containing a fluid obtained from a person or animal, measuring or detecting one or more characteristics of the fluid, and displaying an indication relating to the measurement. FIG. 8B is an exploded view of the indicator 800. Indicator 800 has a generally tubular housing 814 and an end cap 822. The indicator 800 has a distal end 810 on the housing and a proximal end 818 on the end cap 822. End cap 822 serves to close and seal the housing 814 and furnishes a fluid flow connection to the fluid flow path 816. A fluid flow passage 816 extends between respective intake and outflow ports at the distal end 810 and the proximal end 818. A diffuser 840 is disposed in an enlarged chamber or portion 820 of the fluid flow passage 816. An indicating element 830 is disposed around the diffuser 840. The diffuser is built up from a plurality of blocks 842 disposed in series. FIG. 8C is an exploded view showing two instances of blocks 842 from which the diffuser 840 is built up. Each block has one or more apertures 844, such that, in the built-up form, the respective apertures 844 of the plurality of blocks 842 are columnar-aligned. Each columnar-aligned group of apertures forms a fluid-flow conduit, passage, or lumen extending the length of the built-up diffuser 840. Spacers 846 provided on the blocks preclude a seal between adjacent blocks, such that fluid may leak in or out of the conduits or lumina. The diffuser 840 seals against the distal end 848 of the chamber 820.

In operation, the intake port at the distal end 810 of the indicator 800 is connected to a fluid transport source, and source of vacuum or suction is applied to the outflow port at the proximal end of the end cap 822. Under the influence of vacuum or suction in chamber 820, fluid is drawn through the distal end port through passage 816 and then through the conduits or lumina in the center of the diffuser 840. Fluid flows from the central conduits or lumina outward through the spaces between blocks 842 toward and in contact with the indicating element 830. The fluid continues along the outer wall of the chamber 820 through the end cap 822 and exits through the proximal end port to the vacuum or suction system.

FIG. 9 is a cross-section view of another example embodiment 900, according to a further aspect of the invention, of apparatus for obtaining and containing a fluid obtained from a person or animal, measuring or detecting one or more characteristics of the fluid, and displaying an indication relating to the measurement. Indicator 900 may be particularly suitable for use where a source of continuous vacuum or suction is not available, where it is desirable to filter the fluid before reaching the indicating element, or where the indicating element is of a type which requires that positive pressure be present to force the fluid to saturate or impregnate the indicator. Indicator 900 has a housing 910 and a diffuser element 918 which may be generally similar to those of the housing 110 and diffuser 120 of FIGS. 1A-1E, with certain exceptions noted hereunder. A distal end 912 provides a port which opens into a fluid passage 914. A proximal end 920 provides a port which opens into a fluid passage or chamber 922. A valve 916 is provided in the passage 914 and permits fluid flow only in the direction from the distal end port to the proximal end port. A plunger 924 is provided in the chamber or passage 922. The plunger 924 may be used to draw or aspirate fluid from a fluid transport source through fluid passage 914 and valve 916 into a chamber 940 in the indicator section 942 of the housing. The plunger 924 may also be used to create positive pressure in the chamber 940 after aspiration of fluid. A filter 932 optionally may be disposed concentrically on the outside of the diffuser in the indicator section. The filter 932, may be used, for non-limiting example, where the fluid under test is whole blood, and it is desirable that only plasma reach the indicating element (108), substantially excluding red blood cells therefrom. The plasma has certain proteins that may adhere to antibodies present in the indicating element—i.e., such that the indicating element is sensitive to certain proteins in the plasma—and cause a color change.

The filter could also exclude particles or other components from reaching the indicator element. The fluid may have components that vary in density, viscosity, flow characteristics, and may bear particulates, solids, or gel globules of various sizes, and other differences. The filter may operate as a mechanical filter such as a mesh, screen, or other media, but could also employ other means of selecting or deselecting or differentially passing components of the fluid, including without limitation electrical charge, magnetic fields, chemical bonds, receptors or other means, fluid dynamics, size, shape, density, viscosity, or the like.

Figure 12A:
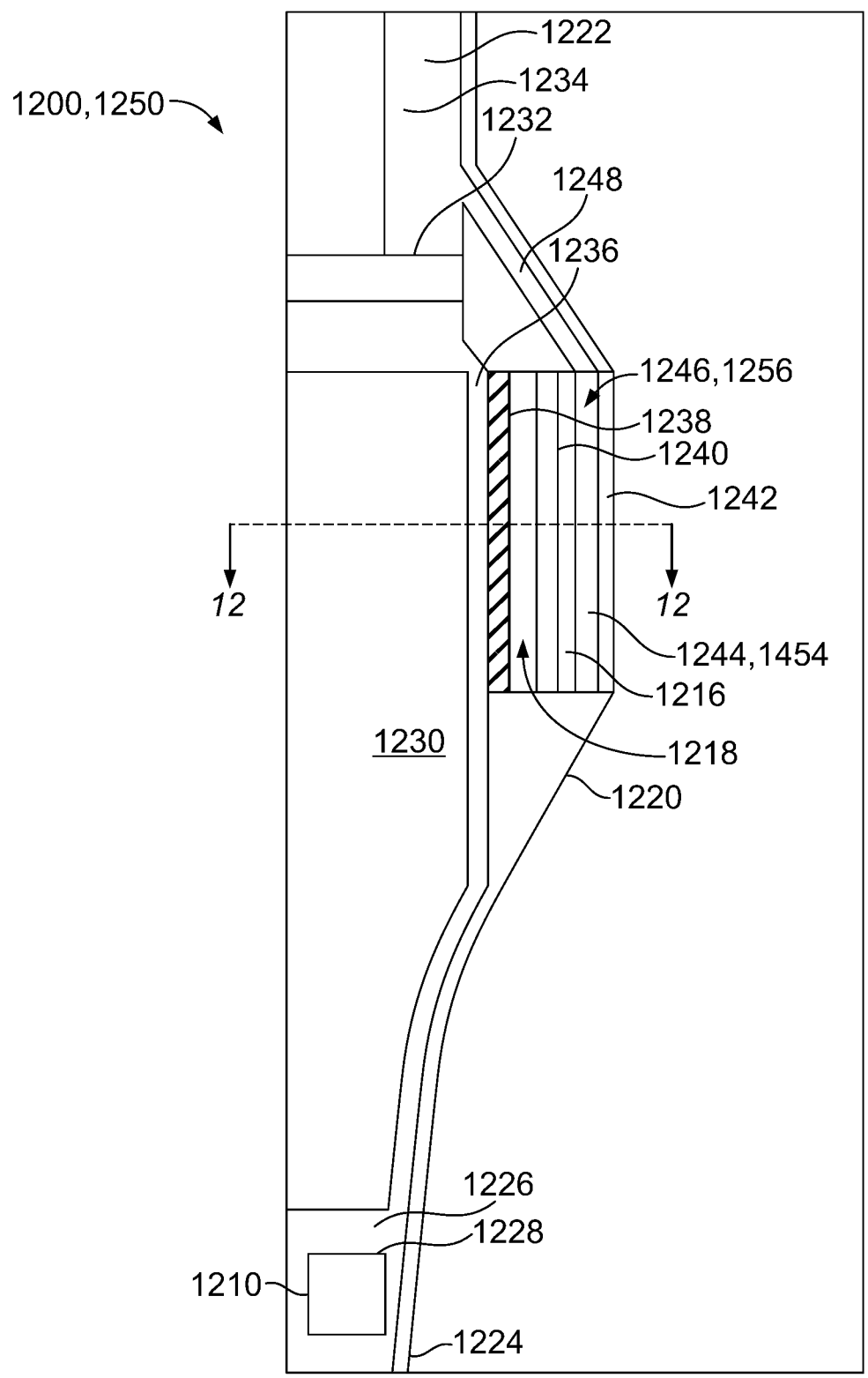
FIG. 12A depicts a simplified schematic cross-section view of further example embodiments 1200, 1250, of an indicator device constructed according to aspects of the invention.
Figure 12B:
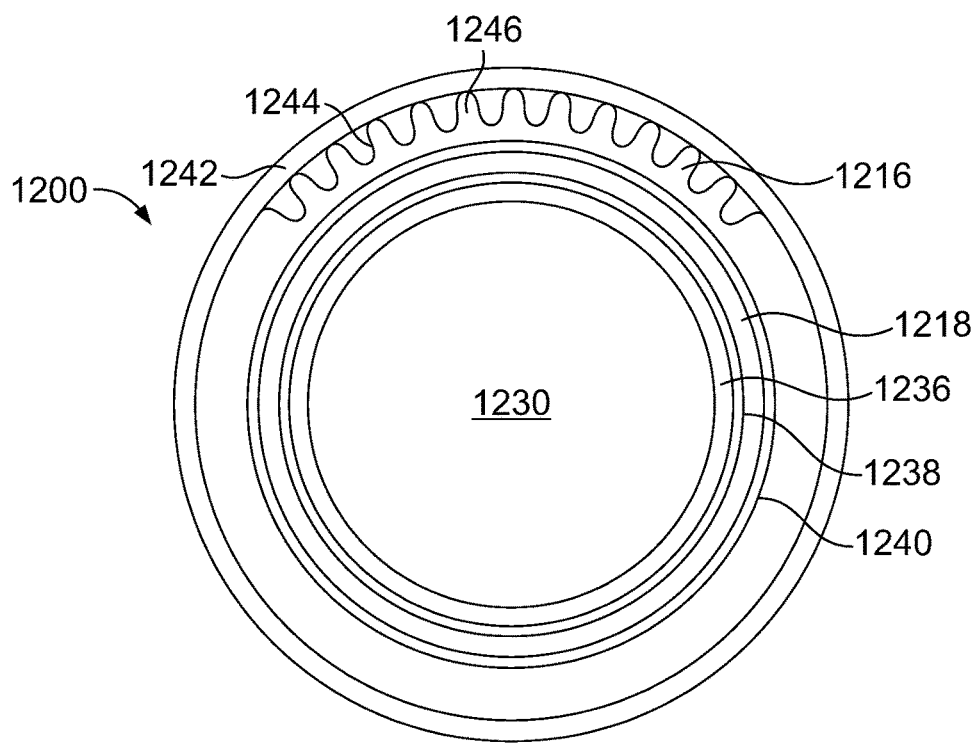
FIG. 12B is a simplified cross-section view of indicator 1200 of FIG. 12A, taken along section line 12-12 of FIG. 12A.
Figure 12C:
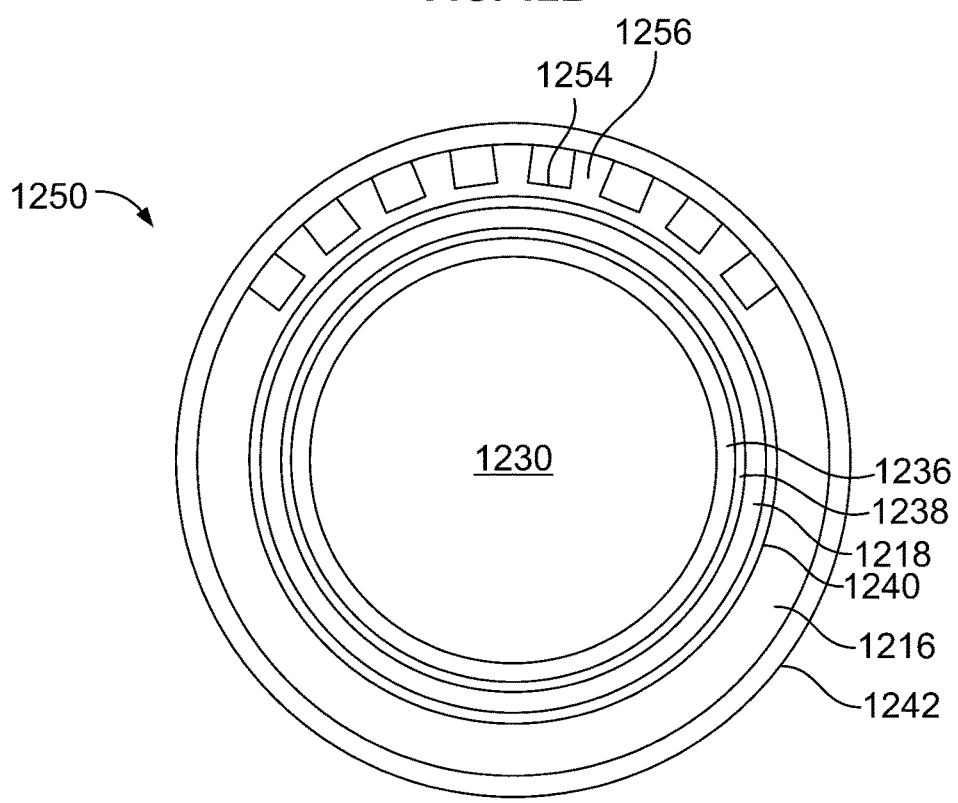
FIG. 12C is a simplified cross-section view of indicator 1250 of FIG. 12A taken along section line 12-12 of FIG. 12A.

An indicating element 934 may further be disposed concentrically on the outside of the filter 932, if present, or outside of the diffuser is no filter is present. The indicating element may be observed through an indicator window 938 and compared to a reference indicator 936 to obtain an indication, reading, or measurement. Pressure created by the plunger 924 forces fluid through the filter and into the indicating element 934. FIGS. 12A, 12B, and 12C depict, in schematic form, a further example embodiment of an indicator having a filter and the capability of using positive pressure in the housing to force fluid though the filter and toward the indicating element. Any of the aforementioned indicators could be modified to incorporate a filter as generally shown in FIG. 9.

The indicating elements, and the measuring components, substances, or media thereof, described for use with the indicators herein, may be realized using any suitable paper, material or device which can measure, sense, or detect a characteristic or property of a fluid and provide a visual or other externally discernible indication of the measurement. In this description of the properties of the indicating elements, it is intended that references to the indicating elements generally also include the measuring components, substance, or media thereof. Moreover, the indicating elements may include without limitation various configurations wherein the indicating element is: (a) formed as a substrate or matrix, which may or may not be permeable, with the measuring components, substance, or media impregnated, entrained, enmeshed, combined, or otherwise disposed therein; (b) formed as a substrate, with the measuring components, substance, ink, matrix, or media applied to, attached to, adhered to, printed on, or otherwise disposed on a surface or embedded in a matrix thereof; or (c) formed as a structure substantially composed of the measuring components, substance, or media, e.g., as a solid, matrix, or gel. The measuring components, substances, or media may be solid or flexible and may be dry or remain wet or tacky during the shelf life of commercial embodiments. Wet or tacky measuring components may be needed or desirable for use in measuring characteristics of particulates, granules, and powders. The indicating element preferably furnishes a visual indication of a chemical property, such as pH, which may, for example, be manifested as a change in color, reflectivity, or the like. The indication may, for example, be represented as a distinguishable one of two well-defined states (for example, the indicator might be red in one state blue in another), or a distinguishable one of a larger plurality of recognizable discrete states, or as an observable point, value, or range along a continuum (or example, the indicator might display a shade of color, within a range of colors).

The shape of the indicator window may act as a magnifying lens to allow a small medium to be easily viewed. The position and size of the indicating element is preferably selected such that the condition of the indicating element is visually apparent when fluids are initially aspirated or drawn into the indicator so that the user need not take any additional steps in order to obtain a measurement. For example, when an indicator is used in an application where pH is sensed to confirm correct insertion of the nasogastric tube in the patient's stomach, the sizes and positions of the indicating element and indicator window are preferably selected so that the pH indication (or a simpler correct insertion indication that the pH is below a threshold which condition is accepted as evidence of correct insertion) is clearly observable to a user upon or shortly after aspiration of the fluid sample in the indicator without requiring the user to undertake additional steps to ascertain the measurement. However, in other applications, the user may be required to perform one or more additional operations or manipulations of or related to the indicator in order to obtain a measurement.

Any appropriate chemical-property indicating devices, media, measuring components, or substances including but not limited to litmus, pH indicating strips, paper, cloth, or any other substrate impregnated with or bearing a pH indicator, or the like, may be used to implement the indicating element.

The indicator may generally be used to obtain a measurement of the gastric pH. This measurement may be employed for purposes in addition to establishing correct insertion of a nasogastric tube, including, without limitation, determination that the stomach is prepared to receive a therapeutic agent, or that an appropriate quantity of a therapeutic agent affecting pH, has been introduced. As an alternative to a pH-sensitive medium, media indicating chemical properties other than pH, which may verify correct insertion of a nasogastric tube, signal incorrect insertion of a nasogastric tube, or verify correct or sufficient introduction of a therapeutic, buffering, or irrigation agent, could also be used. The indicators and indicating elements may be used with fluids other than gastric aspirates, including without limitation blood, plasma, and gases, and may be used with such fluids including particulates, granules, powders and other solids that may be entrained therein.

The indicating element may also be sensitive to other properties, such as the presence or activity of certain proteins, such as a paper with antibodies that react or provide an indication responsive to the presence or absence of the proteins. Any protein for which an indicative antibody or other sensing substance is available could be the target of the indicating element. For one non-limiting example, the indicator may sense the presence of Troponin in concentrations above a threshold. Troponin is a protein found in higher concentrations during a myocardial infarction, and thus, an indicator equipped with an indicating element sensitive to Troponin could be useful clinically to provide a rapid determination of that condition, allowing for more immediate treatment. Moreover, the indicating element may be sensitive to other substances or properties, including without limitation, genetic markers, toxins, drugs (e.g., acetaminophen), albumin, human chorionic gonadotropin (HCG), any substance for which an immunoassay is available, or any other substance or property.

The indicating element may furnish a simple indication, such as a color, throughout the indicating element or an exposed or saturated part thereof. The indicating element may also display shapes, letters, icons, symbols, or other indicia in addition to or instead of colors, and the measurement or indication may by represented or distinguished by position, orientation, or quantity of indicia, or some visible change in appearance (or other detectable change) of the indicating element. For non-limiting examples, the indication or measurement may be provided as the appearance (or absence) of a word or phrase (e.g., "OK", "STOP", etc.), the quantity of visible symbols, the quantity of symbols which are a particular or have undergone a change in color, the highest or lowest of several displayed numbers, the highest or lowest of several numbers which have undergone a change in color, a recognizable pattern of indicia, or the like. The indicating element may also bear a plurality of measuring components, substances, or media. The plurality of measuring components, substances, or media may be sensitive to different respective properties or substances. These may be juxtaposed or organized in groups or patterns so as to present measurements by way of combinations or cooperation of several indicia or components. Thus, different measuring components, substances, or media may overlap or be adjacently arranged, so that the measurement indication is presented as a composite or blended color, or distinguishable patterns or symbols, or the like. Other arrangements could also be used.

A suitable reference indicator, such as reference indicators 116 of FIGS. 1A, 1D, and 1E, 546 of FIG. 1F, or 936 of FIG. 9 may be provided to guide a user in interpreting the indications provided by the indicating element. In some cases, the number, pattern or complexity of the indications which may be displayed by the indicating element does not permit a comprehensive guide to interpretation to be presented in the space available on the reference indicator provided on the housing or other component of the indicator. Plural reference indicators may be provided on the housing or other component of the indicator. Also, the on-device reference indicator may be replaced by, or supplemented by, a separate reference indicator, which could be, for example, a card, nomogram, pamphlet, or the like.

FIG. 10A is a flow chart of an example embodiment of a method 1000 which may be used in conjunction with embodiments of indicators of the types disclosed herein for obtaining a measurement or detection of one or more characteristics of a fluid acquired from a person or animal. The method 1000 may be used with a "source" of vacuum or suction external to the indicator device. Although the several steps of method 1000 are shown in a particular order, some of the steps may be executed in a different order, and some of the steps may be omitted, including some steps which are not explicitly characterized as optional.

In step 1010, the user couples the indicator's intake port to a fluid transport source. This may include attaching a fitting on the fluid transport source to a mating fitting at the intake port, and where the transport source and the intake port are not directly compatible, may include the use of an adaptor, such as adaptor 700 or a similar adaptor. In step 1012, the user couples the indicator's outflow port to a source of vacuum or suction. The source may, for example, be a tube or other conduit connected to a vacuum or suction system. The vacuum or suction source could also be a suction bulb or syringe or a tube or conduit coupled thereto. This may include attaching a fitting on the outflow port to a mating fitting on the suction source. Where vacuum or suction source and the outflow port are not directly compatible, this may include the use of an adaptor, such as adaptor 700 or a similar adaptor.

In step 1014 the user enables the source of vacuum or suction so as to cause fluid to be drawn into the indicator. This step is optional, in that the vacuum or suction may continuously operate. Controlling the vacuum or suction may be preferable in some applications to avoid having continuous flow past the indicator. As an alternative, a valve could be provided at or near the intake port of the indicator or in the fluid transport source, allowing the user to control the flow of fluid through the indicator. If the source of vacuum or suction is a bulb or syringe, the user may operate the bulb or syringe to cause the fluid to be drawn into the indicator.

In step 1016, the user observes the presence of fluid in or past the indicator. This step is optional. In step 1018, which is optional, the user disables the flow of vacuum or suction, or otherwise stops the flow of fluid through the indicator.

In step 1020, the user obtains a measurement displayed or exhibited or otherwise detectable from the indicator. For example, if the indicating element is operative to display a color change responsive to the presence or amount of a characteristic of the fluid, the user may observe the color of the indicator element, e.g., through the window, and compare it with the reference indicator to obtain the measurement. The measurement could also be obtained by an instrument that senses the display or other reaction of the indicating element. The term "measurement" may include the determination of a continuous-valued result that represents the characteristic (e.g., 5.5), or the determination of a range within which the result falls (e.g., in the range 5 through 6), the determination that the result exceeds a threshold (or does not) (e.g., below 6), the determination that the result corresponds to a specific indication displayed by the indicating element (e.g., the displayed characters "OK"), or another appropriate determination.

In step 1022, the user uncouples the intake and outflow ports from the fluid transport source and the source of vacuum or suction, respectively. In step 1024, the user may safely dispose of the indicator and accessories.

FIG. 10B is a flow chart of an example embodiment of a method 1050 which may be used in conjunction with embodiments of indicators of the types disclosed herein for obtaining a measurement or detection of one or more characteristics of a fluid acquired from a person or animal. The method 1050 may be used with an indicator device that incorporates a syringe or other accessory element to produce suction or vacuum, and pressure, in the indicator device. Method 1050, may be used, for example, with indicator 900 of FIG. 9 and indicators 1200, 1250 of FIGS. 12A, 12B, and 12C. Although the several steps of method 1050 are shown in a particular order, some of the steps may be executed in a different order, and some of the steps may be omitted, including some steps which are not explicitly characterized as optional.

In step 1060, the user depresses the plunger of the syringe (or similar accessory) to ready it for use in drawing fluid into the indicator. In step 1062, the user couples the indicator's intake port to a fluid transport source. This may include attaching a fitting on the fluid transport source to a mating fitting at the intake port, and where the transport source and the intake port are not directly compatible, may include the use of an adaptor, such as adaptor 700 or a similar adaptor.

In step 1064, the user ensures an intake valve is open to allow fluid to be drawn from the fluid transport source. The intake valve may be provided as part of the indicator near the intake port thereof, or in accessory tubing or conduits. This step is optional. In some applications, the valve may not be required. And some valves may operate automatically to allow fluid to flow in only one direction, to enter the indicator, through the intake port.

In step 1066, the user withdraws the plunger of the syringe to draw fluid from the fluid transport source through the intake port and into the indicator. The user may stop operating the plunger when sufficient fluid is observed to occupy the indicator to saturate the indicating element.

In step 1068, the user ensures that the intake valve is closed. This step is optional, as the valve may not be required or may operate automatically.

In step 1070, the user depresses the plunger so as to force fluid through a filter and into contact with or the vicinity of the indicating element. If the intake valve is present, it prevents fluid from exiting through the inflow port, and in conjunction with the operation of the plunger, causes the pressure in the interior of the indicator to increase, thereby forcing the fluid through the filter. If the intake valve is not present, the movement of the fluid under the influence of the plunger may be sufficient to cause fluid to flow through the filter.

In step 1072, the user obtains a measurement displayed or exhibited or otherwise detectable from the indicator. For example, if the indicating element is operative to display a color change responsive to the presence or amount of a characteristic of the fluid, the user may observe the color of the indicator element, e.g., through the window, and compare it with the reference indicator to obtain the measurement. The measurement could also be obtained by an instrument that senses the display or other reaction of the indicating element.

In step 1074, the user uncouples the intake port from the fluid transport source. In step 1076, the user may safely dispose of the indicator and accessories.

FIGS. 11A through 11E are simplified cross-section diagrams of several example embodiments of indicating elements, and configurations thereof, which may be used in conjunction with any of the indicators disclosed in this application.

Figure 11A:
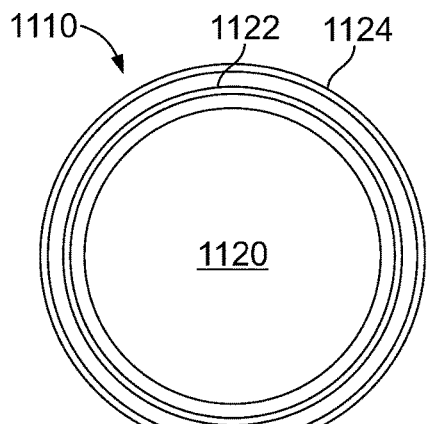
FIG. 11A is a simplified cross-section diagram of an example embodiment 1110 according to an aspect of the invention showing an arrangement of an indicating element 1122 formed as a tube or rolled section of a material having the measuring capability, and certain other components thereof.

FIG. 11A depicts an example embodiment 1110 having an indicating element 1122 with a general configuration similar to that previously disclosed in connection with indicator 100 of FIGS. 1A, 1D, and 1E. The indicating element 1122 is constructed as a tube or cylinder and is disposed generally coaxially between diffuser 1120 and the generally tubular wall 1124 of the housing. The housing wall 1124 may be transparent to form a window through which the indicating element may be observed. The indicating element 1122 may, for non-limiting example, be realized as a tube or rolled section of a pH-indicating paper. In this configuration, the measuring component or medium, which may for non-limiting example be a pH-sensitive material that changes color responsive to pH, is impregnated as an integral part of the indicating element 1122. Other measuring components or media could also be used as hereinbefore described. The indicating element 1122 could be entirely composed of the measuring component or medium, instead of being formed as a substrate with the measuring component or medium impregnated therein.

Figure 11B:
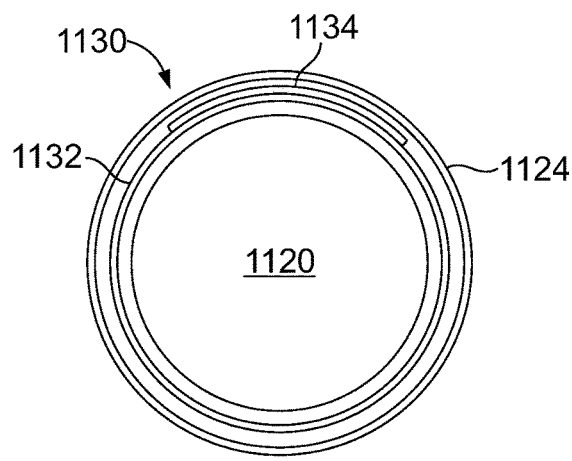
FIG. 11B is a simplified cross-section diagram of an example embodiment 1130 according to an aspect of the invention showing an arrangement of an indicating element 1132, wherein the measuring component or medium is disposed on an outer surface of a tubular substrate, and certain other components thereof.

FIG. 11B depicts an example embodiment 1130 having an indicating element 1132 with a general configuration similar to that of indicating element 1122 of FIG. 11A. The indicating element 1132 may constructed as a tubular or cylindrical substrate and is disposed generally coaxially between diffuser 1120 and the generally tubular wall 1124 of the housing. However, the measuring component or medium 1134 is disposed on the outer surface of the indicating element 1132. The measuring component or medium 1134 may, for example, be a gel, ink, or other appropriate indicating substance, and may be deposited, printed, adhered with adhesive, or otherwise applied or attached to the indicating element 1132 substrate.

Figure 11C:
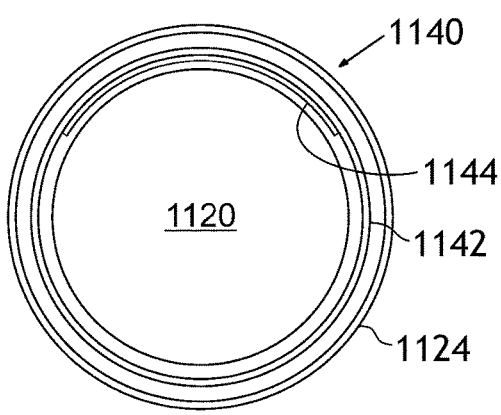
FIG. 11C is a simplified cross-section diagram of an example embodiment 1140 according to an aspect of the invention showing an arrangement of an indicating element 1142, wherein the measuring component or medium is disposed on an inner surface of a tubular substrate, and certain other components thereof.

FIG. 11C depicts an example embodiment 1140 having an indicating element 1142 with a general configuration similar to that of indicating element 1122 of FIG. 11A. The indicating element 1142 may constructed as a tubular or cylindrical substrate and is disposed generally coaxially between diffuser 1120 and the generally tubular wall 1124 of the housing. However, the measuring component or medium 1144 is disposed on the inner surface of the indicating element 1142. The measuring component or medium 1144 may, for example, be a gel, ink, or other appropriate indicating substance, and may be deposited, printed, adhered with adhesive, or otherwise applied or attached to the indicating element 1142 substrate. The indicating element 1142 is preferably transparent or translucent so that the state of the measuring component or medium 1144 may be observed by the user. Because the visible side of the measuring component or medium 1154 is opposite the side which is exposed to the fluid under test, it is preferably either permeable to the fluid or sufficiently thin or transparent that the effect of the fluid on the exposed side can be observed on the visible side.

Figure 11D:
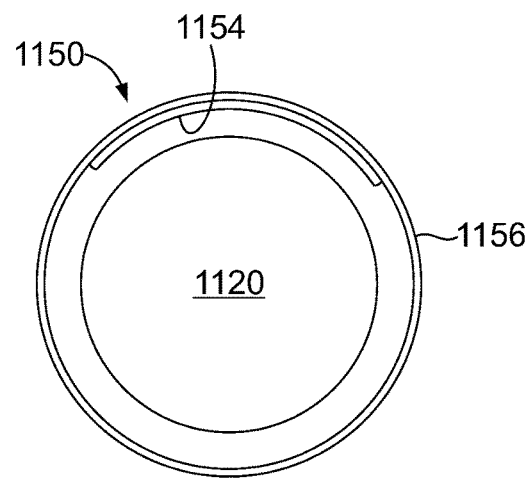
FIG. 11D is a simplified cross-section diagram of an example embodiment 1150 according to an aspect of the invention showing an arrangement wherein the measuring component or medium is disposed on the inner surface of the wall 1156 of the housing.

FIG. 11D depicts an example embodiment 1150 in which the measuring component or medium 1154 is disposed on the inner surface of the generally tubular wall 1156 of the housing, which wall 1156 is disposed generally coaxially about the diffuser 1120. Because the measuring component or medium 1154 is disposed on the inner surface of the wall 1156, a separate substrate need not be provided to support the indicating element (as indicated by the X marks drawn through the substrate in the figure). The measuring component or medium 1154 may, for example, be a gel, ink, or other appropriate indicating substance, and may be deposited, printed, adhered with adhesive, or otherwise applied or attached to the inner surface of wall 1156. Because the visible side of the measuring component or medium 1154 is opposite the side which is exposed to the fluid under test, it is preferably either permeable to the fluid or sufficiently thin or transparent that the effect of the fluid on the exposed side can be observed on the visible side.

Figure 11E:
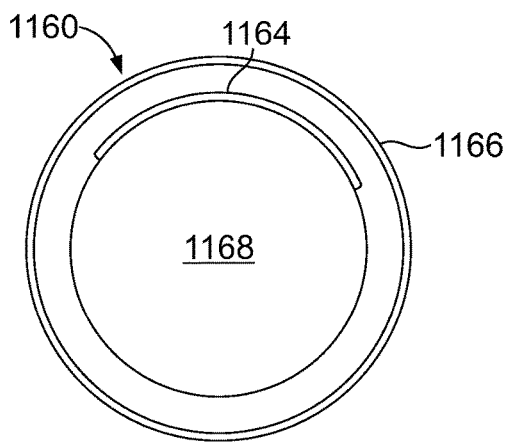
FIG. 11E is a simplified cross-section diagram of an example embodiment 1160 according to an aspect of the invention showing an arrangement wherein the measuring component or medium is disposed on the outer surface of the diffuser 1168.

FIG. 11E depicts an example embodiment 1160 in which the measuring component or medium 1164 is disposed on the outer surface of the diffuser 1168. Because the measuring component or medium 1164 is disposed on the diffuser 1168, a separate substrate need not be provided to support the indicating element (as indicated by the X marks drawn through the substrate in the figure). The measuring component or medium 1164 may, for example, be a gel, ink, or other appropriate indicating substance, and may be deposited, printed, adhered with adhesive, or otherwise applied or attached to the diffuser 1168. The measuring component or medium 1164 is preferably visible through the generally tubular wall 1166 of the housing, which wall 1166 is disposed generally coaxially about the diffuser 1168.

In FIGS. 11B, 11C, 11D, and 11E, the measuring components or media are shown as occupying or covering only a small portion of the circumference of the substrate. However, the measuring components or media may occupy or cover any portion of the substrate, including the entire circumference.

FIG. 12A depicts a simplified schematic cross-section view of further example embodiments 1200, 1250, constructed according to aspects of the invention, of apparatus for obtaining and containing a fluid obtained from a person or animal, measuring or detecting one or more characteristics of the fluid, and displaying an indication relating to the measurement. Indicators 1200, 1250 are generally similar to indicator 900 of FIG. 9 and may be particularly suitable for use where a source of continuous vacuum or suction is not available, where it is desirable to filter the fluid before reaching the indicating element, or where the indicating element is of a type which requires that positive pressure be present to force the fluid to saturate or impregnate the indicator. Indicators 1200, 1250 are similar to one another, differing in the shapes of certain channel-forming structures 1244, 1254 and the drain channels 1246, 1256 formed thereby. FIG. 12A is a view looking toward a sectioning plane extending through a central longitudinal axis of the indicators 1200, 1250. FIG. 12A depicts a half of the view, the reflection about reflection line 1210 providing the otherwise-identical other half. FIG. 12B is a simplified cross-section view of indicator 1200, and FIG. 12C is a simplified cross-section view of indicator 1250, taken along section line 12-12 of FIG. 12A.

Indicators 1200, 1250 have a generally elongate tubular body 1220 with a distal end 1224. The body 1220 defines an interior space including an interior fluid passage 1226 and an indicator section 1236 thereof. The body 1220 provides an intake port leading into the fluid passage 1226 near the distal end 1224. A valve 1228 is optionally disposed in the interior fluid passage 1226 to control fluid passing through the port and the fluid passage 1226. Valve 1228 may be any suitable manually operated valve, such as a stopcock, ball valve, butterfly valve, clamped flexible tube, or the like. Valve 1228 may also be any suitable automatically operating valve that permits fluid to flow through passage 1226 substantially only one-way, into the indicator. For example, valve 1228 may be a flap valve, a needle valve, a duckbill valve, check valve, or any other appropriate valve. A diffuser 1230 of any of the types disclosed heretofore may be disposed in fluid passage 1226.

Fluid passage 1226 preferably includes a syringe section 1222 disposed near the proximal end of the body 1220. A plunger 1234 having a piston 1232 in the syringe section 1222 may be operated to provide positive pressure or negative pressure (suction or partial vacuum) in the fluid passage 1226 on the distal side of the piston.

A filter 1238 may be provided to define a filtered fluid passageway and chamber 1218 to the radial outside of the filter. An indicating element 1240 is preferably disposed in the chamber 1218. Filter 1238 may, for example, be a fluid-permeable cylindrical filter disposed generally coaxially with the diffuser 1230 and the body 1220, and interposed between fluid passage 1226 and chamber 1218, allowing fluid to pass therebetween. The filter 1238 may be constructed using any appropriate filter medium as needed to allow those fluid components to which it is desired to expose the indicating element 1240 to pass, while excluding undesired fluid components. The filter 1238 may be used, for non-limiting example, where the fluid under test is whole blood, and it is desirable that only plasma reach the indicating element, substantially excluding red blood cells therefrom. The indicating element may be sensitive to certain proteins in the plasma. The filter could also exclude particles or other components from reaching the indicator element. The indicating element 1240 may, for example, be a cylindrical element disposed generally coaxially with the diffuser 1230 and the body 1220, to the radial outside of filter 1238.

One or more fluid-channel forming structures 1244 (FIG. 12B) or 1254 (FIG. 12C) are preferably provided on or the interior of the wall 1242 in the area of indicator section 1236. Structures 1244 and 1254, may, for example, be constructed as longitudinal ribs, ridges, striations, or corrugations, forming fluid channels 1246 between the individual ones of the structures. As best seen in FIG. 12B, structures 1244 may have rounded edges. As best seen in FIG. 12C, structures 1254 may have square or rectangular cross sections or other similar non-rounded profile. The fluid channels conduct fluid which has flowed through or around indicating element 1240 and is present in the space 1216 to the radial outside of the indicating element 1240 to a drain passage 1248. As best seen in FIG. 12A, drain passage 1248 is constructed to exhaust into the proximal syringe section of fluid passage 1226. However, drain passage 1248 could instead drain to an external drain, such as a drain tube (not shown).

In operation, the plunger 1234 is depressed in the syringe section 1222 to expel the air to the distal side of the piston 1232. Then the indicator 1200 or 1250 is coupled to the fluid transport source. The plunger 1234 is withdrawn to draw fluid through the distal, fluid intake port, valve 1228, and fluid passage 1226, preferably to fill the indicator section 1236 thereof. The valve 1228, if present, is closed to prevent fluid from escaping from the fluid intake port. Then plunger 1234 is again depressed to pressurize the fluid in fluid passage 1226, including indicator section 1236 thereof. If valve 1228 is an automatically-operating valve, it may close when the fluid passage 1226 is pressurized. Under the influence of this pressure, fluid is forced through the filter 1238. The filtered fluid is forced into the areas 1218, 1216 around indicating element 1240, and then through fluid channels 1246, 1256, drain passage 1248, and then into the syringe section 1222 on the proximal side of piston 1232. Thus, fluid channels 1246, 1256 and drain passage 1248 relieve the pressure created by plunger 1234 in fluid passage 1226 by allowing the fluid to escape. The pressure created by plunger 1234 may be needed to overcome resistance to fluid flow of filter 1238.

Figure 13A:
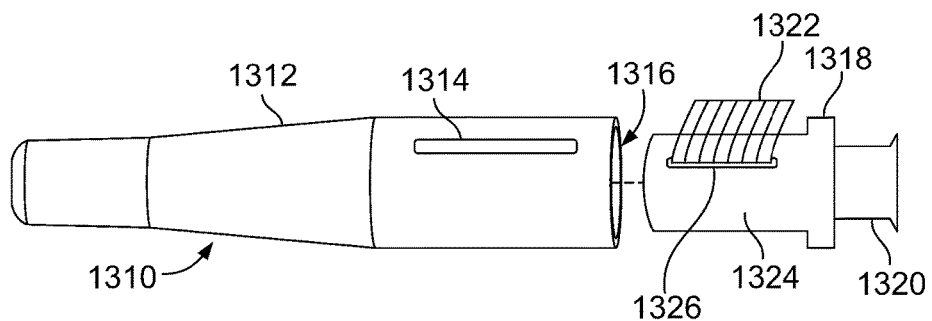
FIG. 13A depicts a partly-exploded side view of a further example embodiment 1310 of an indicator constructed according to aspects of the invention.

FIG. 13A depicts a partly-exploded side view of a further embodiment 1310 of apparatus for obtaining and containing a fluid obtained from a person or animal, measuring or detecting one or more characteristics of the fluid, and displaying an indication relating to the measurement, in accord with a further aspect of the invention. Indicator 1310 is generally similar to the indicator 100 of FIGS. 1A, 1D, and 1E hereinbefore described, with a housing 1312, and a diffuser 1318 which includes a distal, outflow, or exhaust port 1320 for coupling to a source of suction or vacuum. Housing 1312 and diffuser 1318 may be constructed and have functions similar to those of the housing and diffuser of indicator 100. In the assembled form of indicator 1310, diffuser 1318 is telescopically disposed in housing 1312.

The diffuser 1318 preferably has an indicating element 1322 supplied in a quantity larger than that needed for a single use. For example, the indicating element 1322 may be wrapped as a roll of several turns or layers around an outer portion or wall 1324 of the diffuser 1318 that is normally contained within the interior space of the housing 1312. Alternatively, the indicating element 1322 may be formed as a roll of several turns or layers and generally disposed in an interior storage space of the diffuser 1322. The indicating element 1322 may extend through a slit in the wall 1324 of the diffuser and then wrap around a portion of the wall 1324. In operation, fluid in the interior space of the housing 1312 exposes the part of the indicating element 1322 that is on the outside of wall 1324. A gasket or other seal may be provided at the slit to prevent fluid from exposing the portion of the indicating element contained within the interior storage space of the diffuser. A further slit 1314 may be provided in the housing 1312. A used or expended portion of the indicating element 1322 may extend through the slit 1314 to the outside of the housing 1312 where it may be examined or discarded. A gasket or seal may also be provided for slit 1314 to avoid leakage of the fluid out of the indicator, or drawing air into the indicator under the influence of vacuum or suction.

The exposed part of the indicating element 1322 could also be viewed through an indicator window (not shown), as with other embodiments of indicators hereinbefore described. The diffuser 1318 may be rotatable with respect to housing 1312 to cause an exposed portion of the indicating element 1322 to appear in the window.

After a measurement is taken, the used or expended portion of the indicating element 1322 may be drawn through the slit 1314 so as to pull an unexposed portion of the indicating element 1322 from the internal storage compartment of the diffuser 1318, readying the unexposed portion for use. Portions of the indicating element 1322 may be defined by perforations, e.g., to allow one or groups of such portions to be easily separated and removed. Measurements using newly-exposed portions of the indicating element 1322 may be observed in rapid succession by repeatedly drawing fresh, unexposed portions of the indicating element into the fluid-filled space inside within the housing. The indicator 1310 may be drained between uses, allowing measurements to be taken at different times.

Figure 13B:
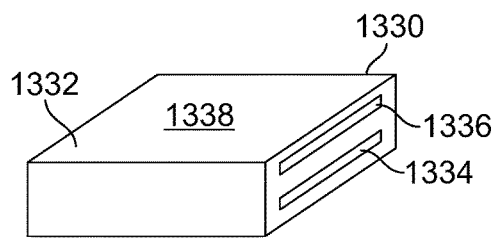
FIG. 13B is a side view of an example embodiment 1330 of a cassette constructed according to an aspect of the invention for storing a supply of indicating element sheets.

FIG. 13B is a side view of an example embodiment 1330 of a cassette constructed according to an aspect of the invention for storing a supply of indicating element sheets. The cassette 1330 could be used in conjunction with the indicator 1310 of FIG. 13A to replace the rolled indicating element 1322. The cassette 1330 could be disposed within the diffuser 1318. Alternatively, a portion of the body of the diffuser could be omitted and the cassette 1330 could occupy that space within the housing 1312. The cassette 1330 may have a body 1332 which houses a supply of indicating element sheets 1334 and 1336. Although two such sheets are shown, the cassette could house any number of sheets. In operation, the sheets may be withdrawn through slits, such as 1314 and 1326, as with indicator 1310. Successive sheets may be folded in an interlocked arrangement so that the complete removal of one sheet causes a limited portion of the following sheet to extend through one or more of the slits to serve as a handle.

Figure 13C:
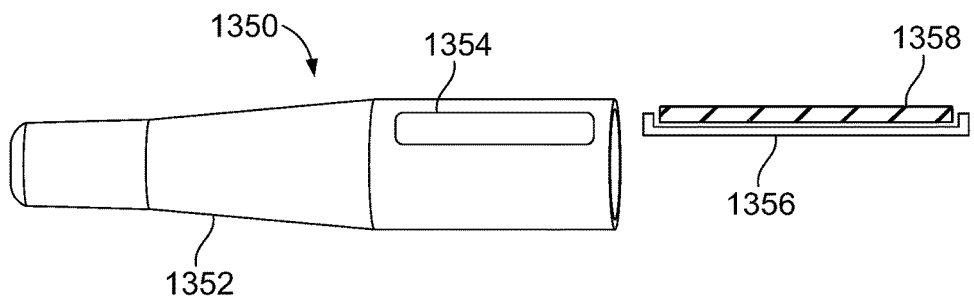
FIG. 13C is a partly-exploded side view of a further embodiment 1350 of an indicator constructed in accord with a further aspect of the invention.

FIG. 13C depicts a partly-exploded side view of a further embodiment 1350 of apparatus for obtaining and containing a fluid obtained from a person or animal, measuring or detecting one or more characteristics of the fluid, and displaying an indication relating to the measurement, in accord with a further aspect of the invention. Indicator 1350 is generally similar to the indicator 100 of FIGS. 1A, 1D, 1E, and 1F, hereinbefore described, with a housing 1352 and a diffuser (not shown). The housing 1352 preferably has an indicator window 1364. An indicating element tray 1356, preferably contains a stacked supply of indicating element sheets 1358, arranged in a manner similar to a printer paper tray. The indicating element tray 1356 may be installed in the housing 1352 so as to be visible in the indicator window 1364. The indicating element sheets 1358 may have a fluid impermeable substrate, and the tray and sheets may be cooperatively arranged so that only the top-most sheet can be exposed by fluid in the interior space of the housing 1350. Expended sheets may be removed, and a new sheet readied for use, by manually removing the diffuser from the housing, and removing the tray 1356 for access. Then the tray and diffuser may be replaced. Alternatively, a slot 1314 may be provided through which the used sheet may extend and be removed.

Figure 13D:
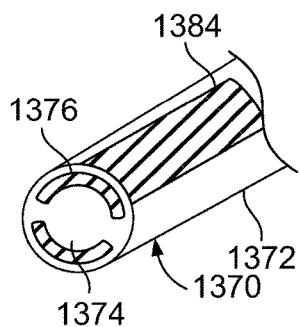
FIG. 13D is a simplified schematic diagram of a further embodiment 1370 of an indicator constructed according to a further aspect of the invention, wherein there is provided a plurality of indicating elements.
Figure 13E:
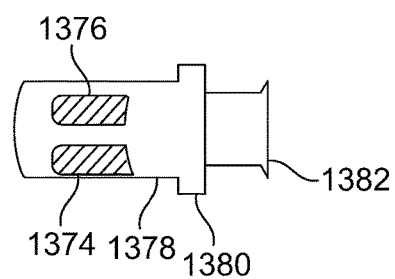
FIG. 13E is a simplified schematic diagram of a further embodiment 1380 of a diffuser constructed according to a further aspect of the invention, and adapted, for example, for use with the indicator 1370 and housing 1372 of FIG. 13D.

FIGS. 13D and 13E depict a further example embodiment 1370 of an indicator which may be constructed according to another aspect of the invention. Indicator 1370 has a housing 1372 which may be constructed in a manner similar to housings of indicator embodiments as hereinbefore described. However, indicator 1370 differs in that housing 1372 preferably has plurality of indicating elements such as 1374 and 1376, and an indicator window 1384 selectively rendering visible a limited subset of the indicating elements, such as indicating element 1376. Housing 1372 preferably also has one or more fluid channels (not shown) adapted to expose to the fluid drawn into the housing only that limited subset of indicating elements visible in the window 1384. Different ones of the indicating elements may thus be selectably exposed to the fluid, observed, and a measurement taken therefrom. FIG. 13E depicts a diffuser 1380 which may be used in conjunction with the housing of FIG. 13D. The diffuser 1380 has a distal or exhaust port 1382 for coupling to a source of suction or vacuum. A body portion 1378 of the diffuser 1380 is adapted for telescopic arrangement in housing 1372. indicating elements 1374 and 1376 are disposed at various angular positions on the body portion 1378. Diffuser 1380 and housing 1372 may be adapted for rotation with respect to one another so as to selectively render visible the indicating elements 1374 and 1376 in the window 1384.

Although the foregoing descriptions of FIGS. 13A-13E refer to diffusers in the form of integrated components having structures to accommodate several functions, including routing the fluid within the housing toward the indicating elements, closing the housing, and containing cassettes, trays, rolls or other supplies of indicating elements, these functions could be provided by separate components.

In some cases, the indicating medium of an indicating element is fragile in some way. For example, some pH papers operate using fluid-characteristic-sensitive dies which can be removed by the action of the fluid passing over or through the paper. The paper itself, once saturated by fluid, can also disintegrate. According to an aspect of the invention, the indicating element may include coatings, membranes, or other structures or treatments to avoid disintegration of the element or its substrate, and avoid separation of the dies or other operating components from the element or its substrate. The chamber or diffuser may also have structures of features to limit fluid velocity or turbulence to minimize disturbance of the indicating element or its substrate.

Figure 14A:
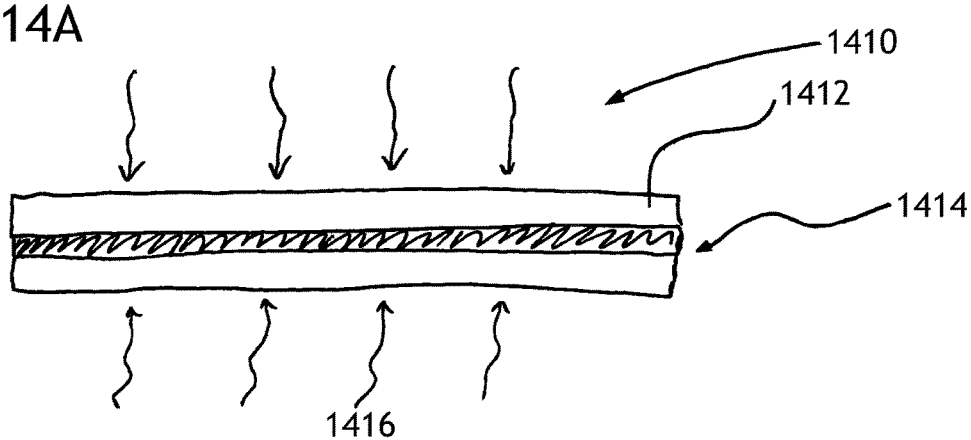
FIG. 14A is a side cross-section view of a further embodiment 1410 of an indicating element constructed according to an aspect of the invention.

FIG. 14A is a side cross-section view of a further embodiment 1410 of an indicating element constructed according to an aspect of the invention. The indicating element 1410 includes an indicating medium 1414, which may for non-limiting example be a pH sensitive paper, but could also be any of the other indicating media or measurement media discussed elsewhere herein. A semipermeable membrane 1412 surrounds the indicating medium 1414. Although the membrane 1412 is shown on both sides of the indicating medium 1414, it could also be provided on only one side, which may be the side facing or exposed to the fluid, or a side that does not face the fluid, if the mechanical arrangement of the indicating element so permits. Fluid 1416 flows through the membrane 1412 to expose or saturate the indicating medium 1414. The membrane may be positioned adjacent to the pH indicator or may form a coating. The membrane helps prevent washing, diluting or dissolving of ph indicator color dye. The membrane can include, but is not limited to, gel, sponge, foam, plastic, and may be formed mechanically, e.g., as a piece of material with micro holes drilled through it). The membrane could also be a stretched PTFE material of the type used in rain clothing. The membrane would also allow gastric fluid to permeate through the barrier to achieve saturation, but provide a mechanical barrier for to prevent dyes from washing out.

Figure 14B:
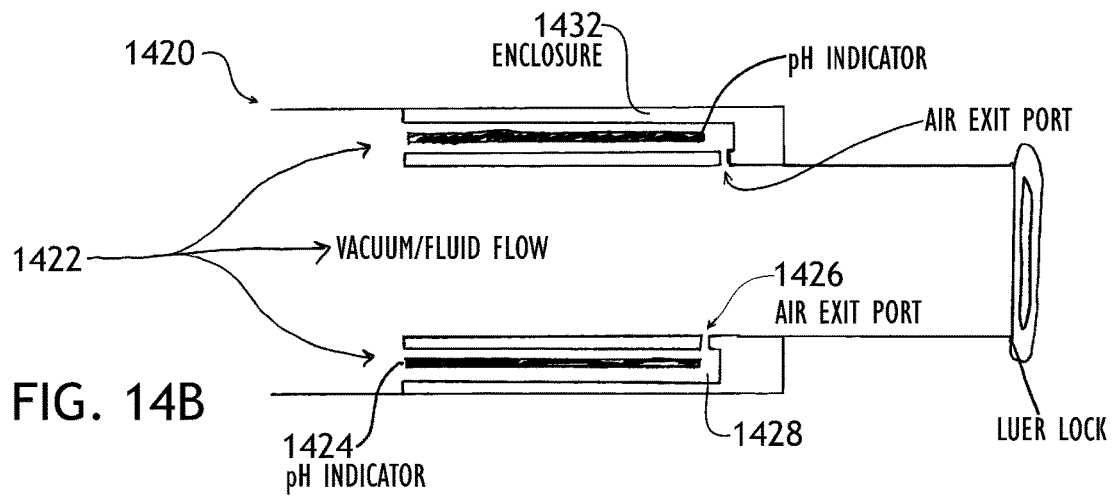
FIG. 14B is a simplified cross-section view of a further example embodiment of an indicator 1420 constructed according to the invention.

FIG. 14B is a simplified cross-section view of a further example embodiment of an indicator 1420 constructed according to the invention, which may be similar to the embodiments of FIGS. 1A, 1D, and 1E but for modifications explained here. The indicating element 1424 is contained in an enclosure 1432 which may be formed as part of the housing or may be a separate piece. The enclosure 1432 forms a space in which the indicating element 1424 resides. In operation, fluid 1422 under vacuum supplied at port 1420 flows through the space or chamber 1428 in which the indicating element 1424 resides. An air exit port 1426 allows air to leave the space, but impedes to at least some extent the flow of fluid, which may also take other paths. Thus the fluid is impeded or retarded in flowing past the indicating element, thereby avoiding disturbing its structure or removing die therefrom.

Figure 14C:
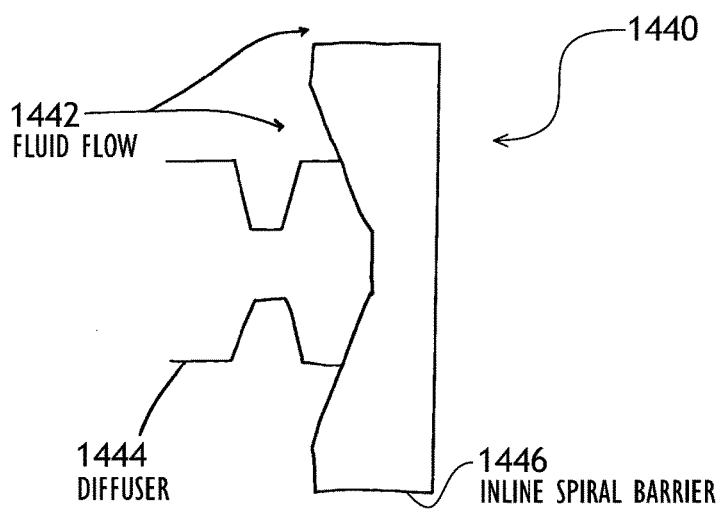
FIG. 14C is a simplified cross section view of a further example embodiment 1440 of an indicator constructed according to the invention.

FIG. 14C is a simplified cross section view of a further example embodiment 1440 of an indicator constructed according to the invention, which may be similar to the embodiments of FIGS. 1A, 1D, and 1E but for modifications explained here. A diffuser of one of the types earlier described is shown at 1444. A mechanical barrier 1446 is provided in the fluid path, and is located closer to the proximal end of the indicator device. The indicator element (not shown) may surround the diffuser. Fluid 1442 flows past the diffuser to expose or saturate the indicator element, but is then stopped or impeded by the barrier 1446, which thereby helps avoid disturbing the structure of or removing die from the indicating element.

In accord with aspects of the invention, plural example embodiments of indicators, and housings, diffusers, end caps and closures have been described herein in several variations. Although some features have been described in the context of particular example indicators, housings, diffusers, end caps, closures, and the like, it is intended that the features may also be applied to other elements of similar function described herein, with no or routine modifications, even though all possible permutations of such features and elements have not been individually mentioned.

What is claimed is:

1. A fluid characteristic indicator comprising:
a housing having a generally tubular body;
a diffuser at least partially disposed in said body;
the housing and the diffuser cooperatively defining a fluid chamber between a distal end of the indicator and a proximal end of the indicator, the fluid chamber adapted to receive fluid at said distal end of the indicator;
said diffuser having at least a first section;
a fluid characteristic indicating element disposed around an outer portion of the diffuser at said first section;
at least a portion of housing body allowing visibility of the fluid characteristic indicating element from the outside of the housing; and
a reference indicator disposed on the outside of the indicator whereby the fluid characteristic indicating element may be compared to the reference indicator.

2. The fluid characteristic indicator of claim 1 wherein:
said housing has a distal end corresponding to said distal end of said indicator;
and an interior surface of the housing has a plurality of fluid guide channels near said distal end of said housing.

3. The fluid characteristic indicator of claim 2 wherein:
said diffuser has a tip section extending into said fluid chamber adjacent said fluid guide channels; and
said tip section of said diffuser is adapted to cooperate with said fluid guide channels to direct fluid entering the fluid chamber at the distal end of the indicator toward said first section of said diffuser.

4. The fluid characteristic indicator of claim 1 wherein said diffuser comprises at least one fluid-channel-forming structure at said first section, whereby at least one fluid channel is formed thereby; and
said indicating element is disposed around the diffuser at said first section.

5. The fluid characteristic indicator of claim 4 wherein said diffuser extends into said fluid chamber; and
said housing and said diffuser cooperate to direct flow of fluid received in said fluid chamber at the distal end of said indicator into said at least one fluid channel toward said indicating element.

6. The fluid characteristic indicator of claim 5 wherein:
said indicating element has a surface facing said diffuser;
said housing, said diffuser, and said fluid channel cooperate to allow fluid to contact said indicating element substantially only on said surface facing said diffuser.

7. The fluid characteristic indicator of claim 5 wherein:
said indicating element has a distal end nearest the distal end of the indicator and a proximal end nearest the proximal end of the indicator; and
said housing, said diffuser, and said fluid channel cooperate to guide fluid flowing through said chamber so as to expose said indicating element progressively from the distal end thereof to the proximal end thereof.

8. The fluid characteristic indicator of claim 5 wherein said diffuser further comprises a transition section between said tip section and said first section, said transition section and said housing being adapted to cooperate to direct fluid from said plurality of fluid guide channels near said distal end of said housing to said at least one fluid channel of said diffuser.

9. The fluid characteristic indicator of claim 4 wherein said at least one fluid channel has a spiral shape.

10. The fluid characteristic indicator of claim 4 wherein said at least one fluid channel has a helical shape.

11. The fluid characteristic indicator of claim 4 wherein said at least one fluid-channel-forming structure is a plurality of fluid-channel-forming structures, said plurality of fluid-channel-forming structures having a star-shaped cross-section, and said plurality of fluid-channel-forming structures forming a plurality of longitudinally-extending fluid channels.

12. The fluid characteristic indicator of claim 4 further comprising a filter disposed between said indicating element and said at least one fluid channel.

13. The fluid characteristic indicator of claim 1 wherein said indicator further comprises a port at the proximal end of the indicator in fluid communication with said fluid chamber, said port being adapted for connection to a source of suction.

14. The fluid characteristic indicator of claim 13 further comprising a channel-forming support disposed in said chamber at a location between said port and said first section of said diffuser, said channel-forming support subdividing said chamber into a plurality of channels.

15. The fluid characteristic indicator of claim 14 wherein said plurality of channels are adapted to substantially evenly distribute vacuum pressure thereamong.

16. The fluid characteristic indicator of claim 1 wherein said diffuser further comprises at least a first locator structure and said housing further comprises at least a second locator structure, said locator structures being adapted cooperate to permit assembly of the diffuser and housing only in a predetermined positional relationship.

17. The fluid characteristic indicator of claim 1 wherein said fluid characteristic indicating element is disposed in a removable tray.

18. The fluid characteristic indicator of claim 1 further comprising a plurality of fluid characteristic indicating elements.

19. The fluid characteristic indicator of claim 18 further comprising an indicator window selectively rendering visible a limited subset of the indicating elements.

20. The fluid characteristic indicator of claim 1 further comprising a plurality of fluid characteristic indicating elements disposed in a removable tray.

21. A diffuser comprising a generally longitudinal diffuser body having a distal end and a proximal end; the diffuser body having:
   a tip section at the distal end;
   a connection tube section forming a tubular fluid passage chamber extending from the proximal end toward the distal end along at least a part of the distance between the proximal end and the distal end; and
   an indicating element section disposed between the tip section and the connection tube section.

22. The diffuser of claim 21 wherein said indicating element section comprises at least one fluid-channel-forming structure, whereby at least one fluid channel is formed thereby.

23. The diffuser of claim 22 wherein said at least one fluid channel has a spiral shape.

24. The diffuser of claim 22 wherein said at least one fluid channel has a helical shape.

25. The diffuser of claim 22 wherein said at least one fluid-channel-forming structure is a plurality of fluid-channel-forming structures, said plurality of fluid-channel-forming structures having a star-shaped cross-section, and said plurality of fluid-channel-forming structures forming a plurality of longitudinally-extending fluid channels.

26. The diffuser of claim 21 wherein said tip section has a diameter is tapered such that the diameter at said distal end is smaller than the diameter adjacent the indicating element section.

27. The diffuser of claim 21 further comprising a tapered transition section disposed between said indicating element section and said tip section.

28. The diffuser of claim 21 further comprising a reference indicator disposed on the outside of the connection tube section of said diffuser body.

29. The diffuser of claim 21 further comprising a channel-forming support between the connection tube section and the indicating element section, said channel-forming support subdividing said fluid-passage chamber into a plurality of channels.

* * * * *